US009898662B2

(12) United States Patent
Tsuda et al.

(10) Patent No.: US 9,898,662 B2
(45) Date of Patent: Feb. 20, 2018

(54) INFORMATION PROCESSING APPARATUS, INFORMATION PROCESSING METHOD, AND INFORMATION PROCESSING SYSTEM

(71) Applicant: SEIKO EPSON CORPORATION, Tokyo (JP)

(72) Inventors: Atsunari Tsuda, Suwa (JP); Toshikazu Uchiyama, Chino (JP); Hitomi Wakamiya, Matsumoto (JP); Masahide Takano, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 147 days.

(21) Appl. No.: 14/901,626

(22) PCT Filed: Jul. 11, 2014

(86) PCT No.: PCT/JP2014/003696
§ 371 (c)(1),
(2) Date: Dec. 28, 2015

(87) PCT Pub. No.: WO2015/008469
PCT Pub. Date: Jan. 22, 2015

(65) Prior Publication Data
US 2016/0148052 A1    May 26, 2016

(30) Foreign Application Priority Data
Jul. 16, 2013   (JP) ................. 2013-147418

(51) Int. Cl.
*G06K 9/00*     (2006.01)
*G06F 19/00*    (2018.01)
(Continued)

(52) U.S. Cl.
CPC .......... *G06K 9/00671* (2013.01); *A61B 34/25* (2016.02); *G02B 27/017* (2013.01);
(Continued)

(58) Field of Classification Search
CPC . G06F 19/3406; G06F 3/012; G06K 9/00671; G02B 27/017; G02B 2027/014;
(Continued)

(56) References Cited

U.S. PATENT DOCUMENTS

2005/0206583 A1*  9/2005  Lemelson .......... A61B 1/00048
                                                    345/7
2006/0071135 A1   4/2006  Trovato
(Continued)

FOREIGN PATENT DOCUMENTS

DE      102010052244 A1   5/2012
EP         2271078 A2     1/2011
(Continued)

OTHER PUBLICATIONS

Apr. 2, 2015 International Search Report issued in International Patent Application No. PCT/JP2014/003696.
(Continued)

*Primary Examiner* — Michelle L Sams
(74) *Attorney, Agent, or Firm* — Oliff PLC

(57) ABSTRACT

An information processing apparatus includes an acquiring unit that acquires a plurality of kinds of medical apparatus information, which are information acquired from a plurality of medical apparatuses, a generating unit that generates information for presentation including at least a part of the plurality of kinds of medical apparatus information acquired by the acquiring unit, and a presenting unit that outputs the generated information for presentation to an image display apparatus that displays an image. The generating unit generates the information for presentation including at least the medical apparatus information acquired by the medical apparatus, visual recognition of a display unit of which by a user of the image display apparatus is difficult.

14 Claims, 15 Drawing Sheets

(51) Int. Cl.
*G02B 27/01* (2006.01)
*A61B 34/00* (2016.01)
*G06F 3/01* (2006.01)
*A61B 90/50* (2016.01)

(52) U.S. Cl.
CPC .......... *G06F 3/012* (2013.01); *G06F 19/3406* (2013.01); *A61B 2090/502* (2016.02); *G02B 2027/014* (2013.01); *G02B 2027/0141* (2013.01); *G02B 2027/0178* (2013.01)

(58) Field of Classification Search
CPC .... G02B 2027/0141; G02B 2027/0178; A61B 2090/502; A61B 34/25
See application file for complete search history.

(56) References Cited

U.S. PATENT DOCUMENTS

| | | |
|---|---|---|
| 2006/0079752 A1 | 4/2006 | Anderl et al. |
| 2006/0082542 A1 | 4/2006 | Morita et al. |
| 2009/0215471 A1* | 8/2009 | Sands .................. G01S 13/876 455/457 |
| 2010/0045580 A1 | 2/2010 | Ichikawa et al. |
| 2010/0046791 A1* | 2/2010 | Glickman ............... G06K 9/209 382/100 |
| 2010/0299627 A1 | 11/2010 | Kenagy |
| 2011/0164163 A1* | 7/2011 | Bilbrey ................. G06F 1/1694 348/333.01 |
| 2012/0013723 A1 | 1/2012 | Laxhuber et al. |
| 2013/0178257 A1* | 7/2013 | Langseth ............... G06T 17/05 463/4 |

FOREIGN PATENT DOCUMENTS

| | | |
|---|---|---|
| EP | 2544039 A1 | 1/2013 |
| JP | 2001104331 A | 4/2001 |
| JP | 2006102495 A | 4/2006 |
| JP | 2010259497 A | 11/2010 |
| JP | 2013034764 A | 2/2013 |
| WO | 2008/026258 A1 | 3/2008 |
| WO | 2011003437 A1 | 1/2011 |

OTHER PUBLICATIONS

Apr. 2, 2015 Written Opinion issued in International Patent Application No. PCT/JP2014/003696.
Azuma, "A Survey of Augmented Reality," Presence, vol. 6, No. 4, Aug. 1997, pp. 355-385.
Vogt et al., "Reality Augmentation for Medical Procedures: System Architecture, Single Camera Marker Tracking, and System Evaluation," International Journal of Computer Vision, 70(2), 2006. pp. 179-190.
Kurakake, S. et al. "Architectures of Application Systems Composed of a Recognition Server and Multiple Camera-Equipped Eyeglass-Based Terminals", the Institute of Image Electronics Engineers of Japan, pp. 1-9.
Gomi, Y., et al. "A Consideration of Using Head Mounted Display on Endoscopic Surgery", Human Interface Society, vol. 10, No. 4, pp. 1-10.

* cited by examiner

[Fig. 1]
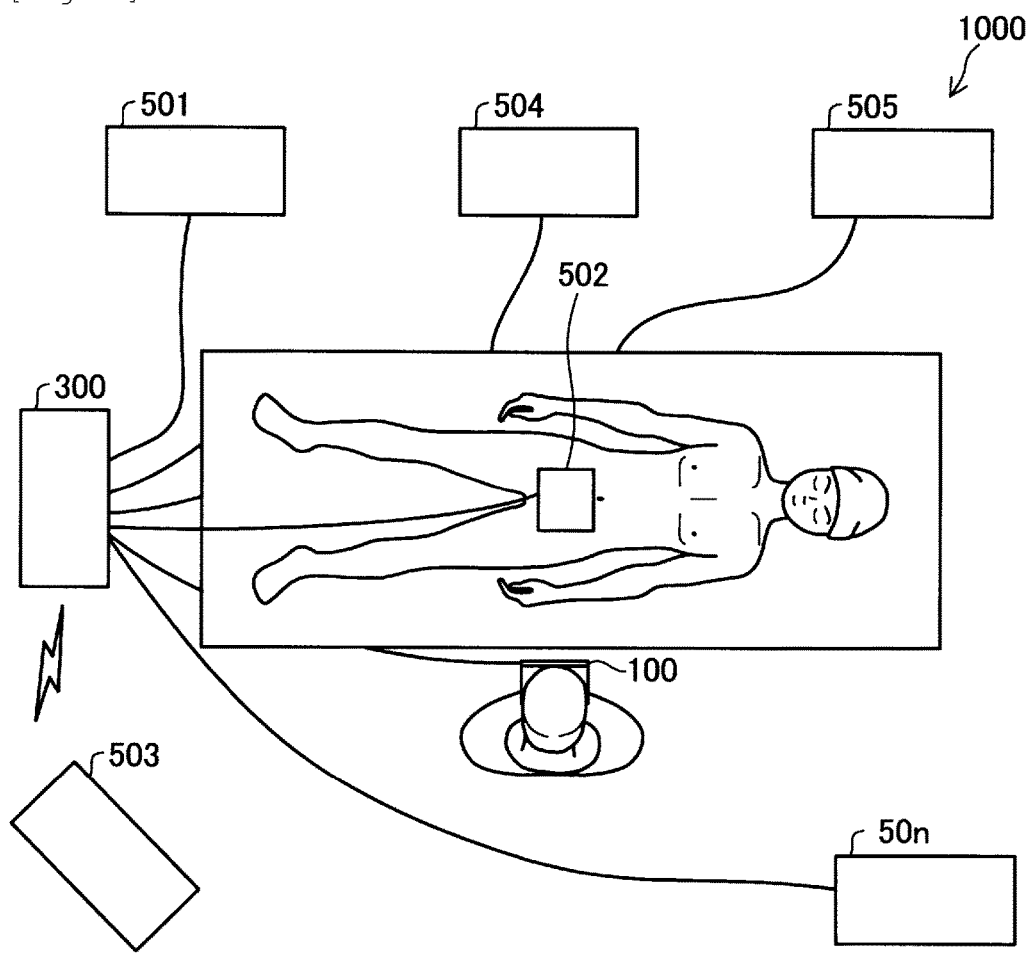

[Fig. 2]
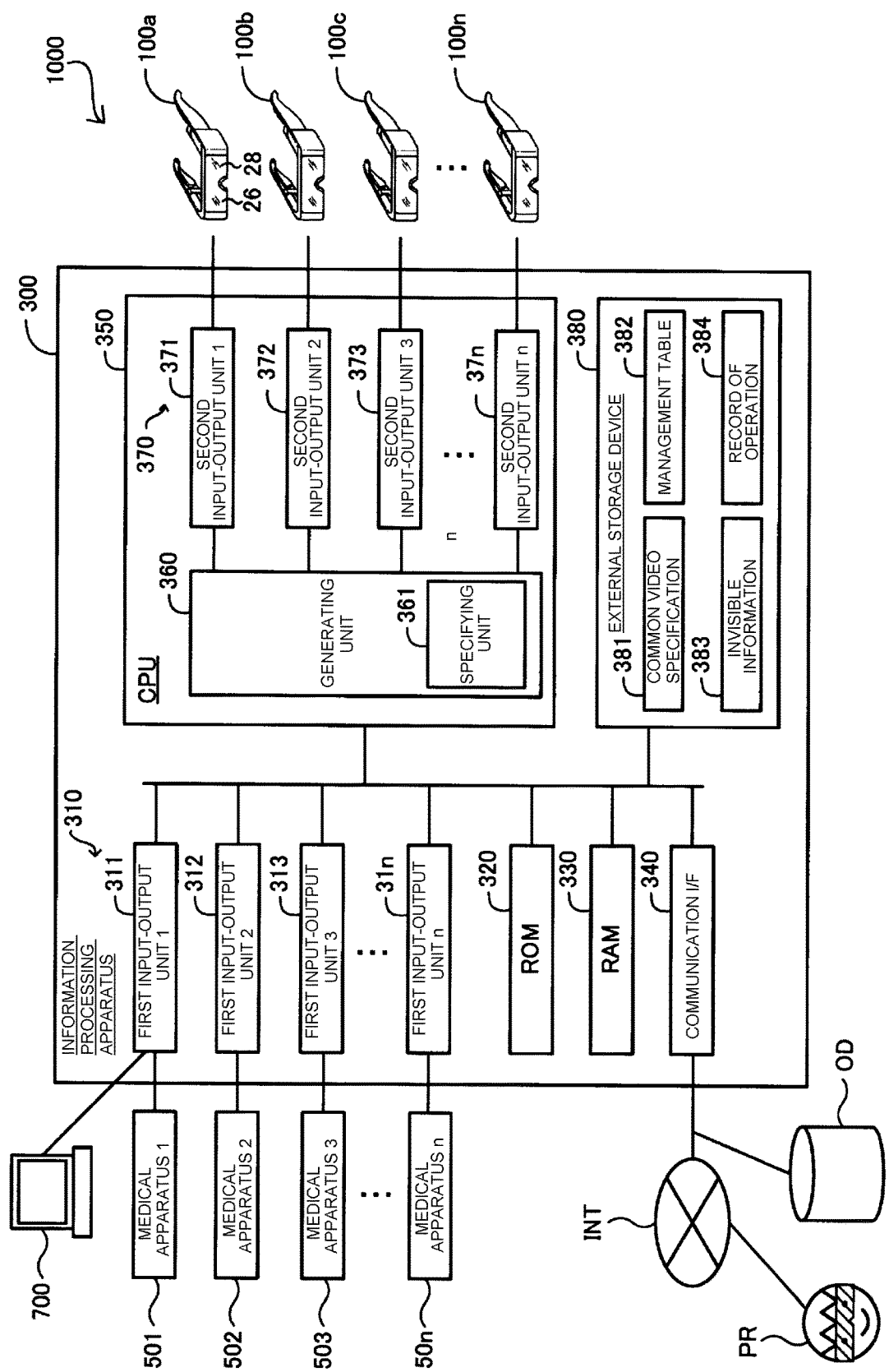

[Fig. 3]

```
                                    ┌─ 381
NUMBER OF PIXELS :     XXX * XX
ASPECT RATIO :         XX : X
RESOLUTION :           XXXdpi
COMPRESSION METHOD :   XXXXXXX

ENCODING METHOD :      XXXX
   ⋮
```

[Fig. 4]

|  | IDENTIFIER | ROLE | VIDEO SPECIFICATION |
|---|---|---|---|
| E01 | 1 | OPERATING SURGEON | SPECIFICATION A |
| E02 | 2 | FIRST ASSISTANT | SPECIFICATION A |
| E03 | 3 | SECOND ASSISTANT | SPECIFICATION B |
|  | ⋮ | ⋮ | ⋮ |
| E0n | n | NURSE | SPECIFICATION E |

382

[Fig. 5]
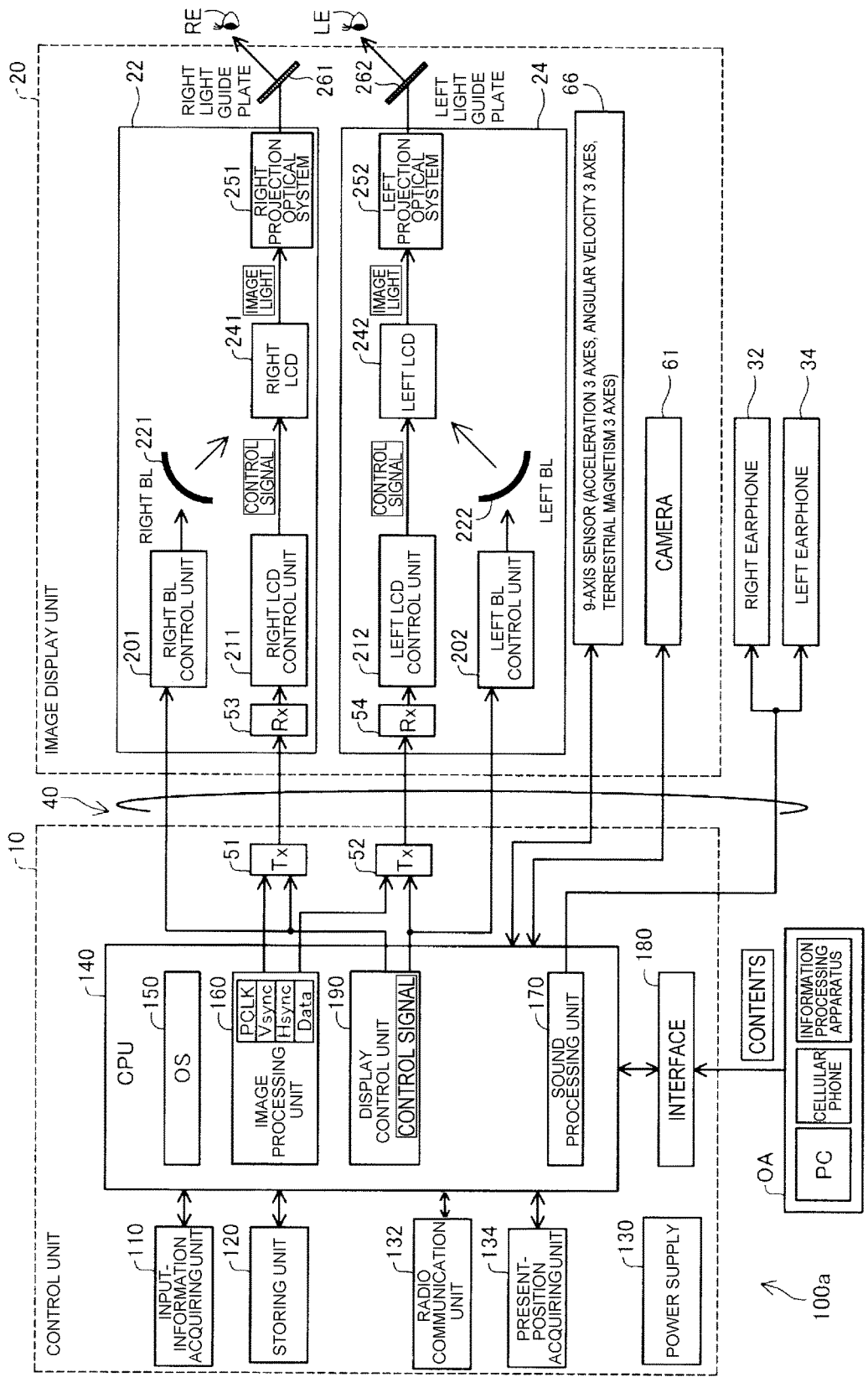

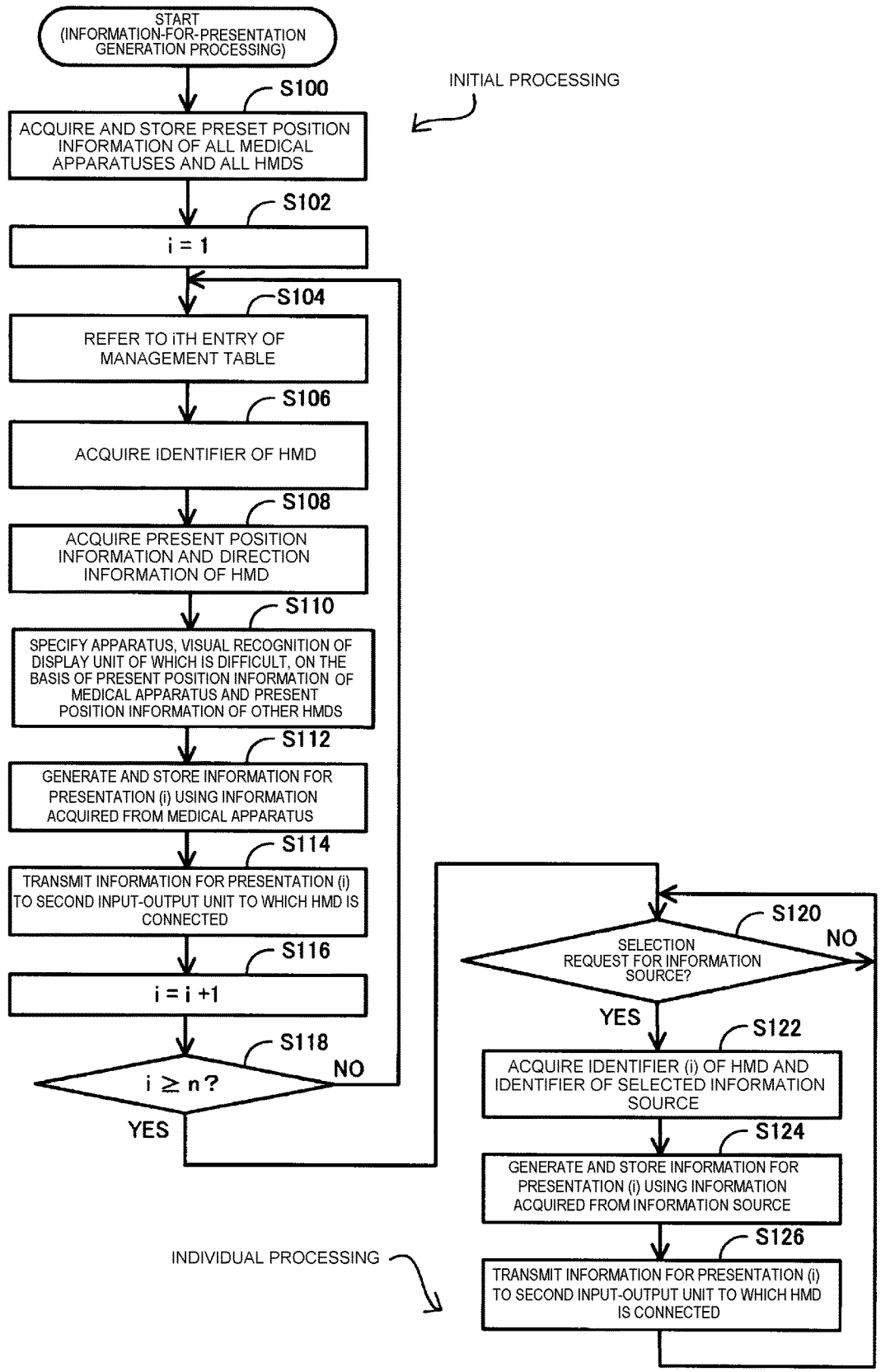
[Fig. 6]

[Fig. 7]
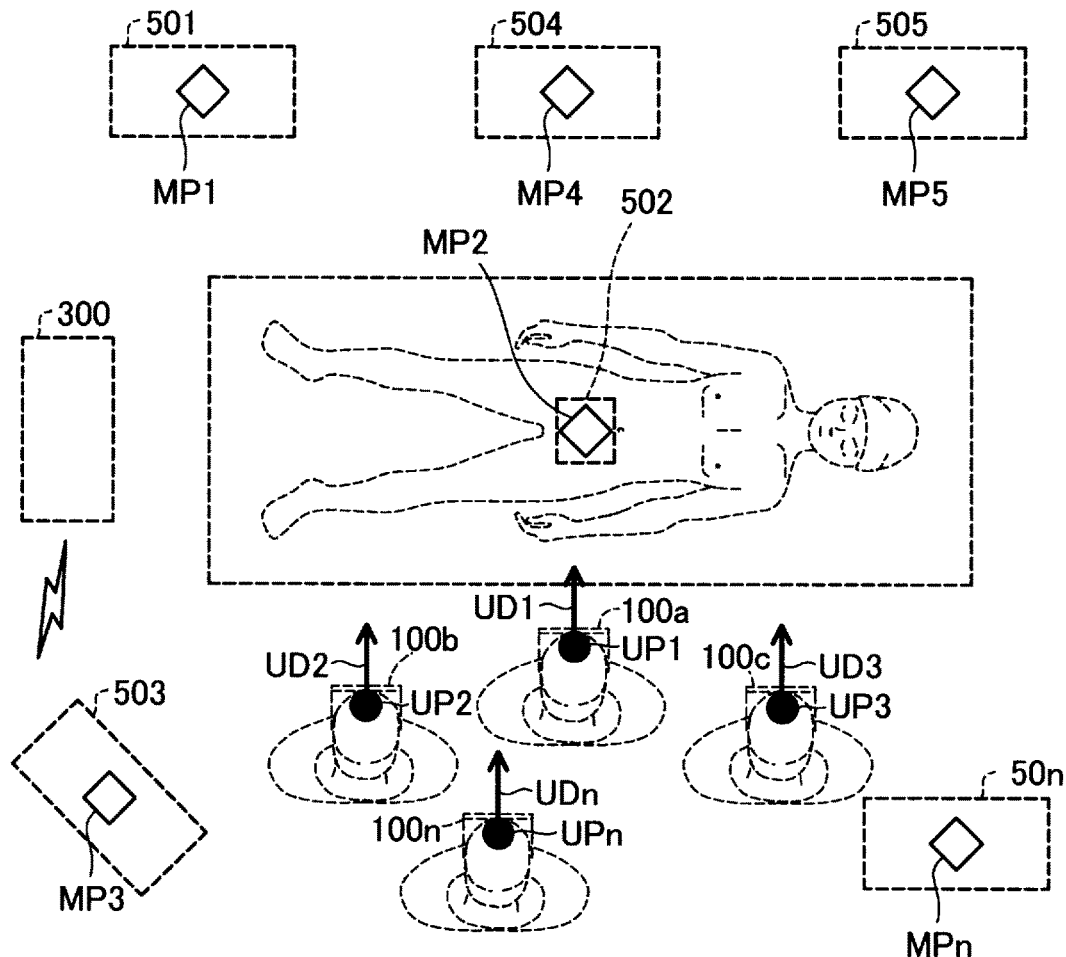
[Fig. 8]
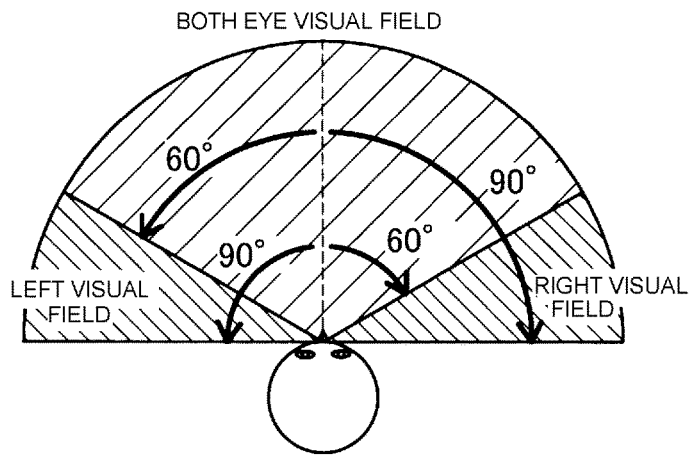

[Fig. 9A]
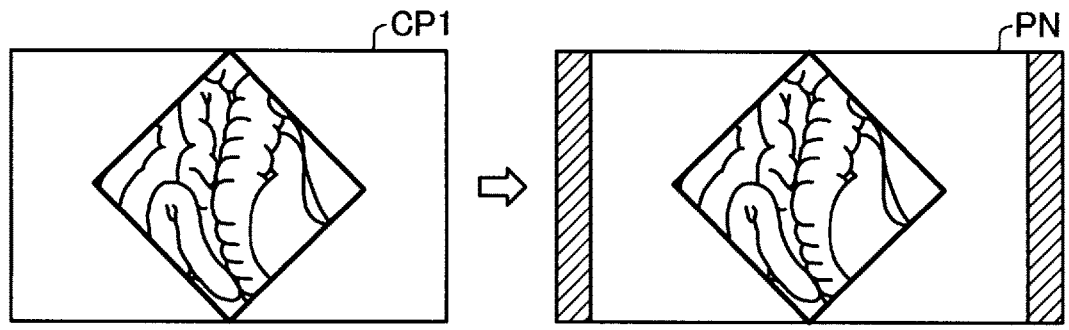
[Fig. 9B]
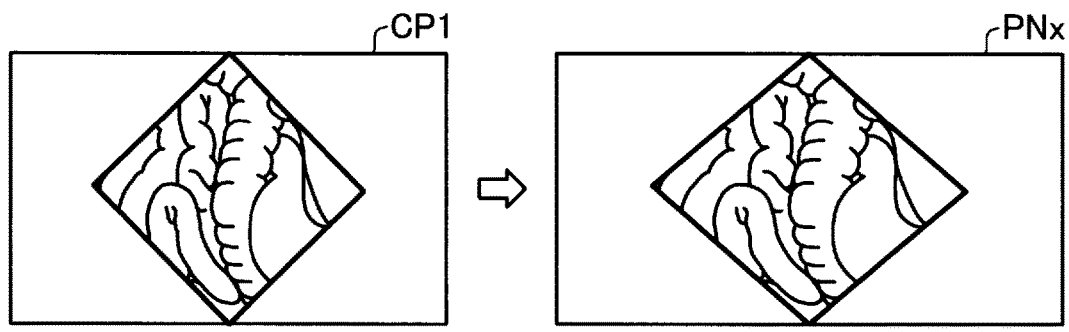
[Fig. 10]
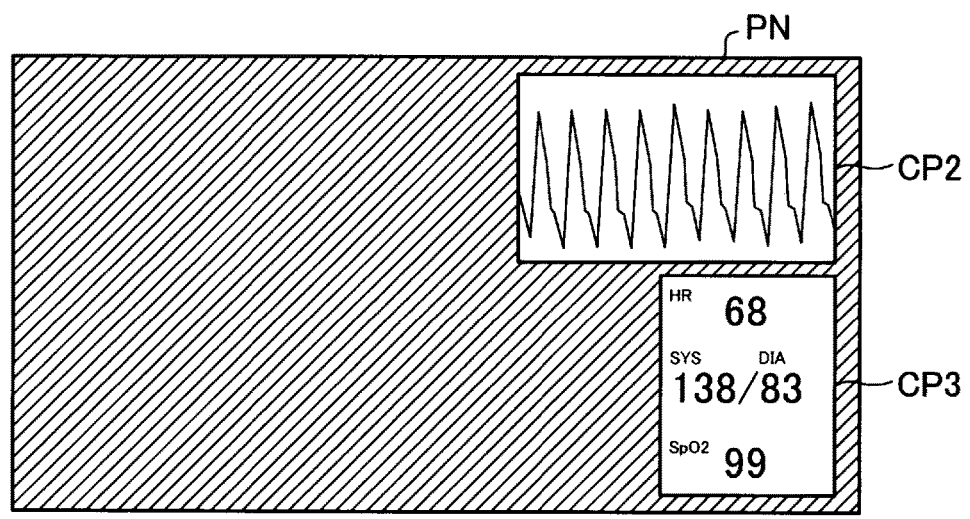

[Fig. 11]
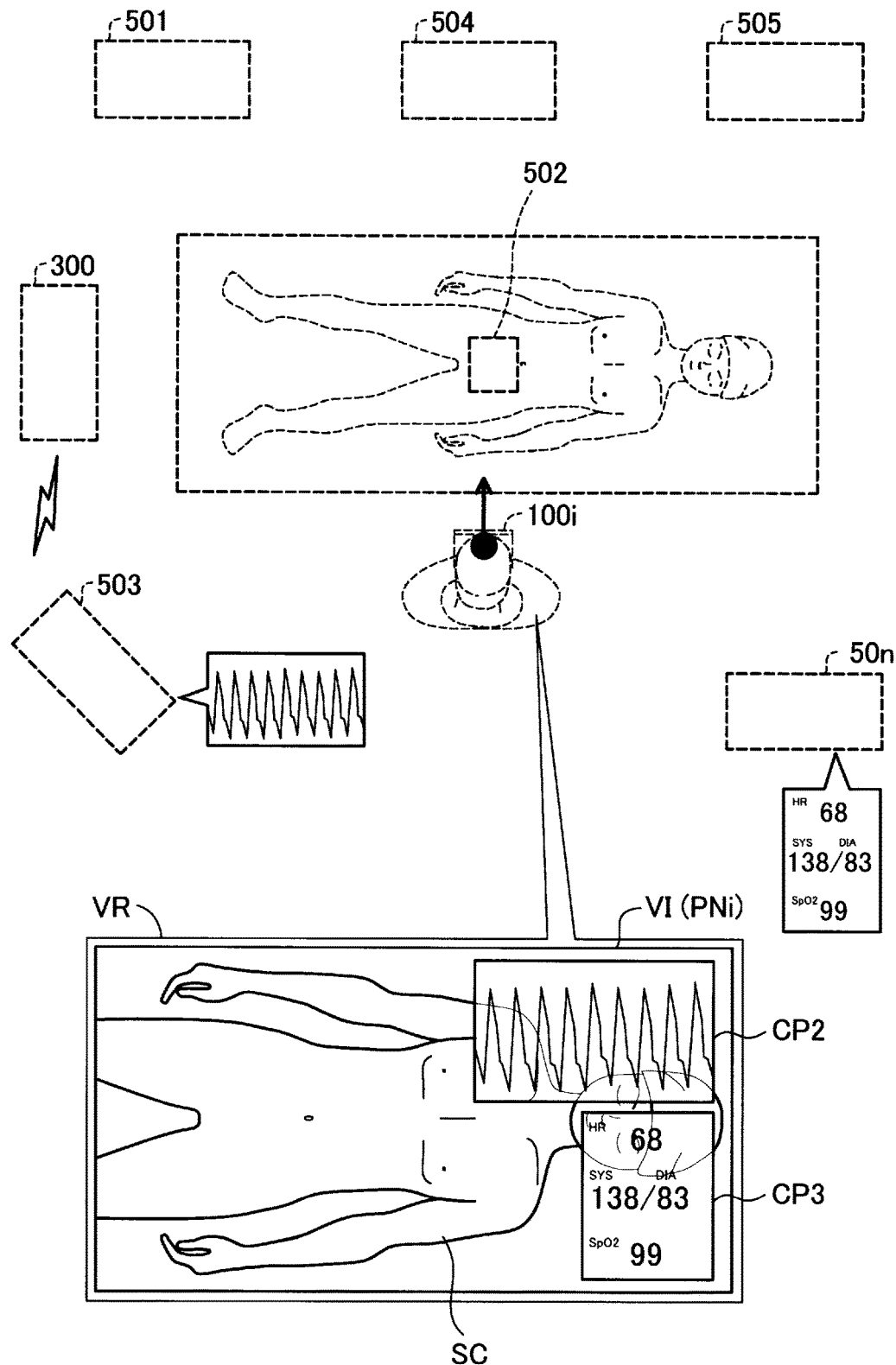

[Fig. 12]
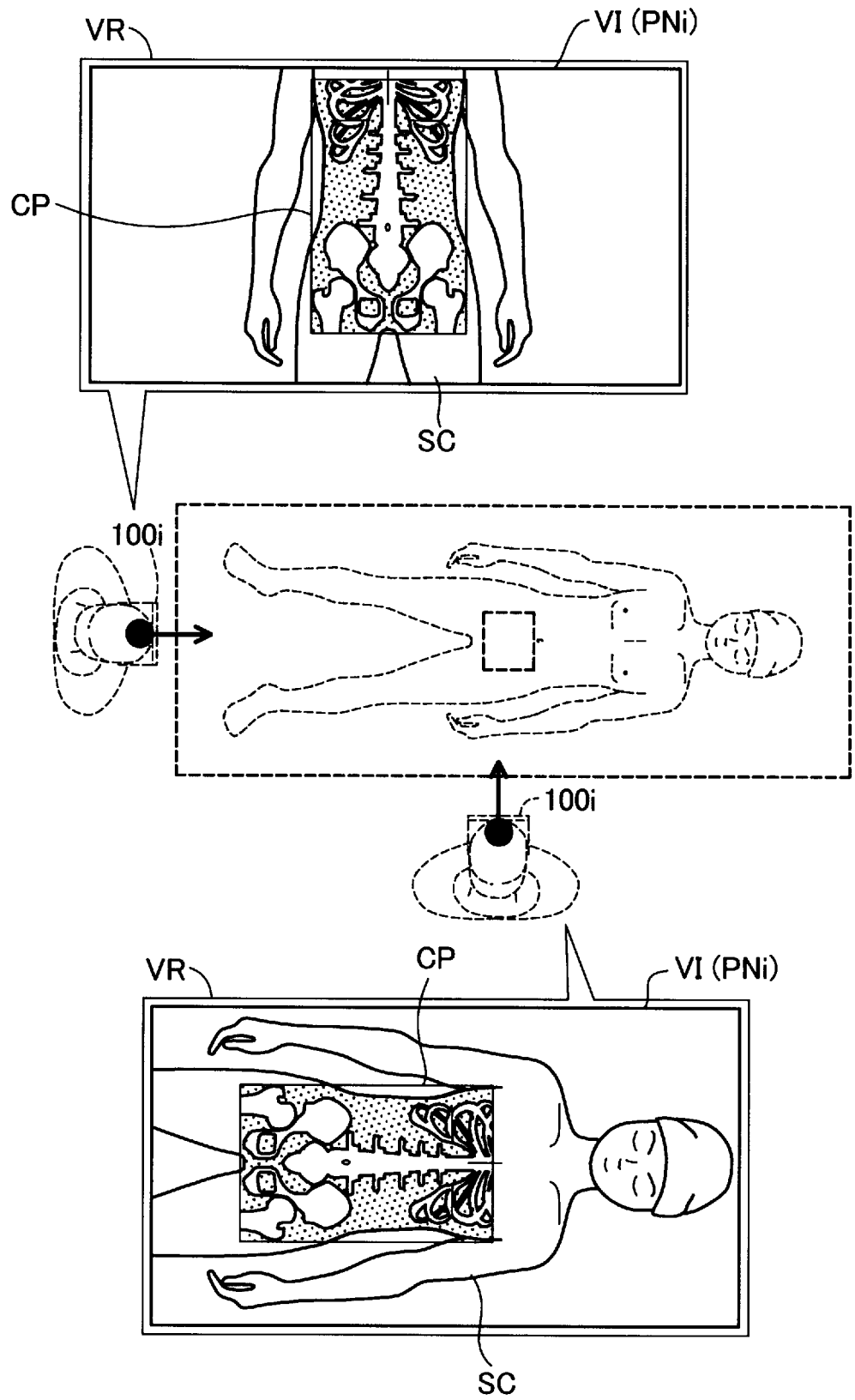

[Fig. 13A]
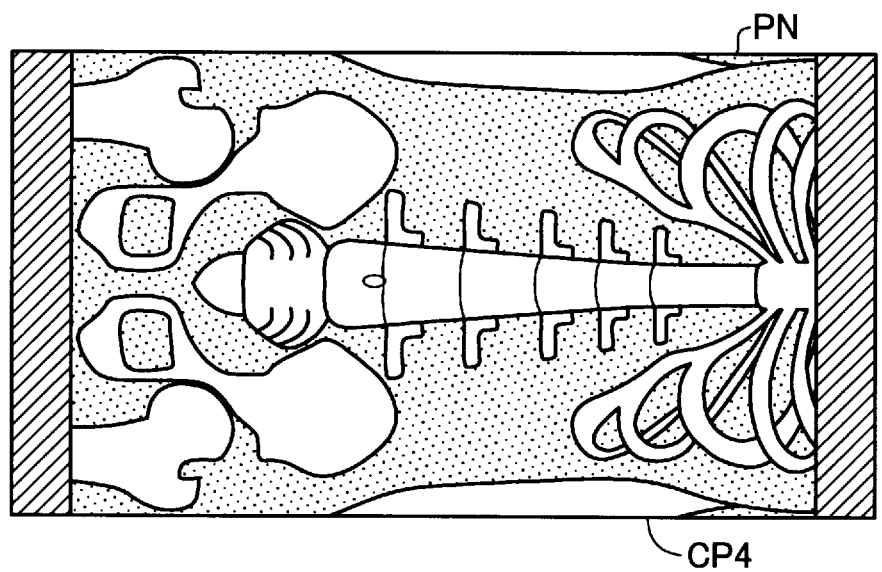
[Fig. 13B]
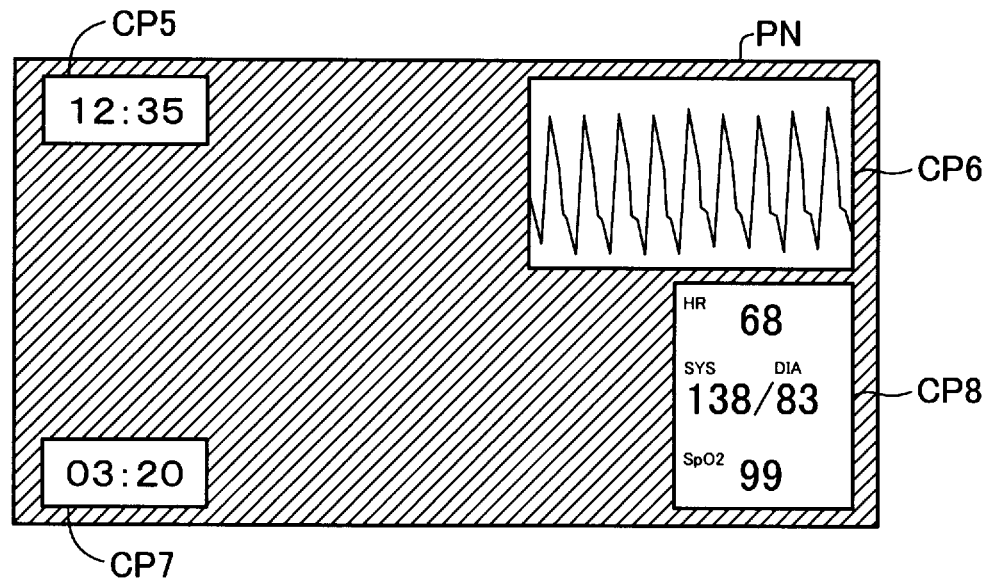

[Fig. 14A]
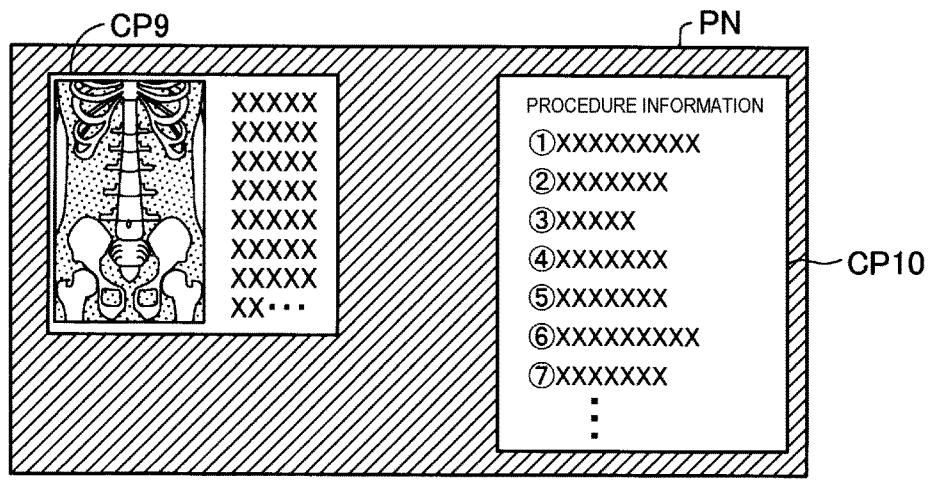
[Fig. 14B]
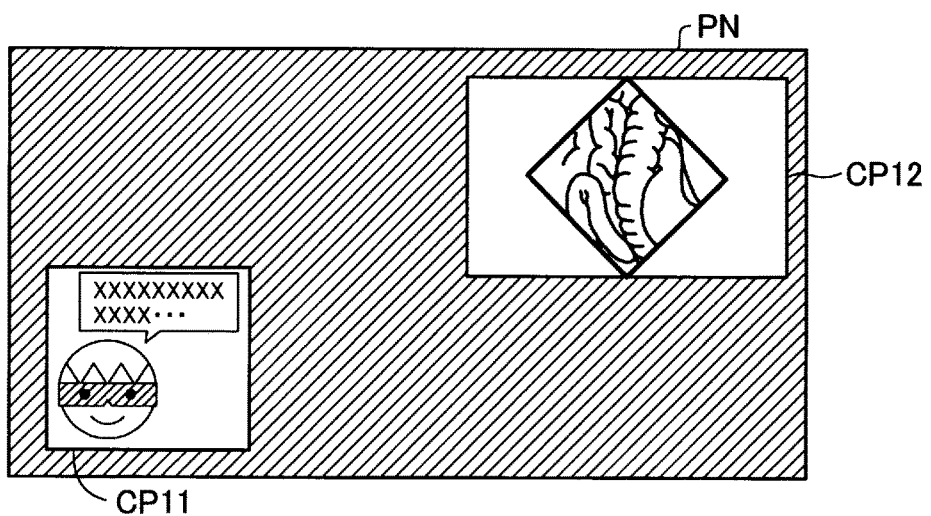
[Fig. 15]
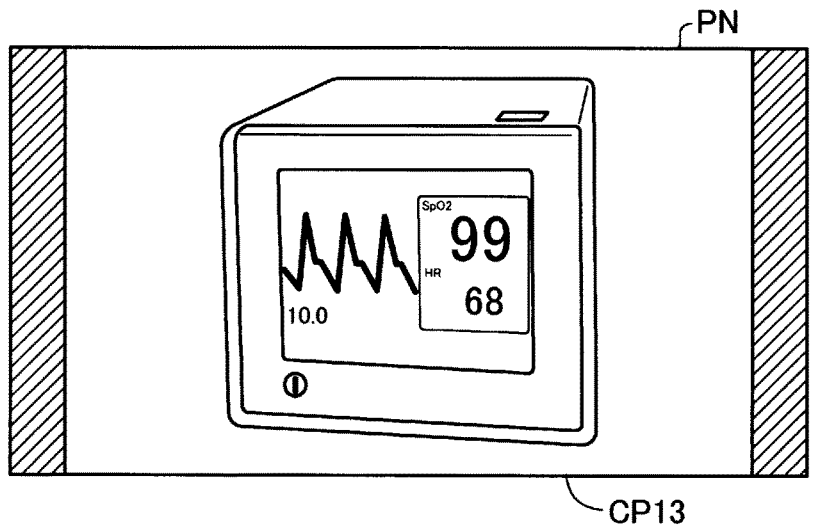

[Fig. 16]
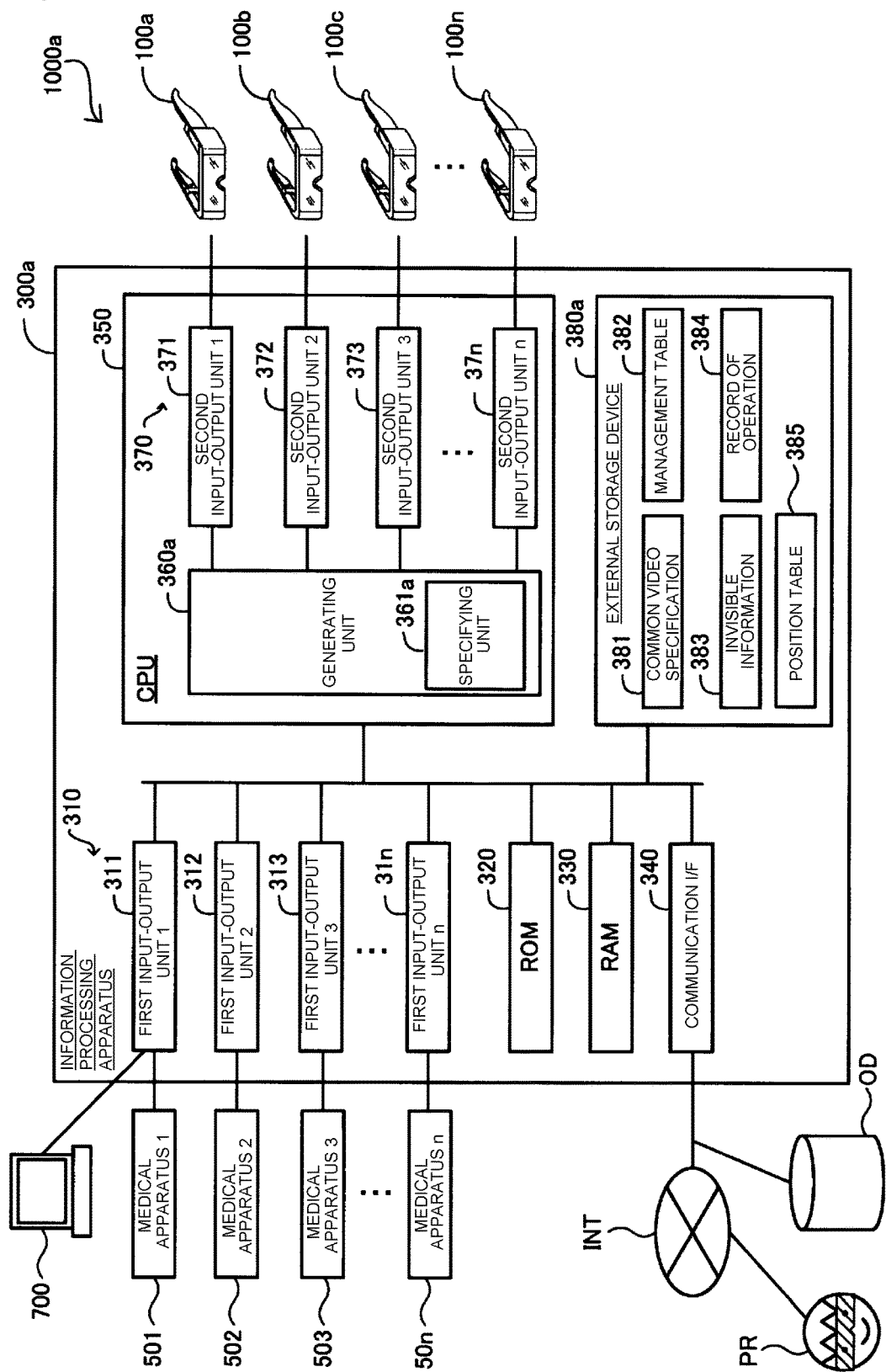

[Fig. 17]

| | IDENTIFIER | APPARATUS 1 | APPARATUS 2 | APPARATUS 3 | APPARATUS 4 | APPARATUS 5 |
|---|---|---|---|---|---|---|
| E01 | 1 | 503 | 50n | | | |
| E02 | 2 | 503 | 505 | 50n | | |
| E03 | 3 | 501 | 503 | 50n | | |
| E04 | 4 | 501 | 502 | 504 | 505 | 50n |
| | ⋮ | ⋮ | ⋮ | ⋮ | ⋮ | ⋮ |
| E0n | n | XXX | XXX | XXX | XXX | XXX |

385

[Fig. 18]
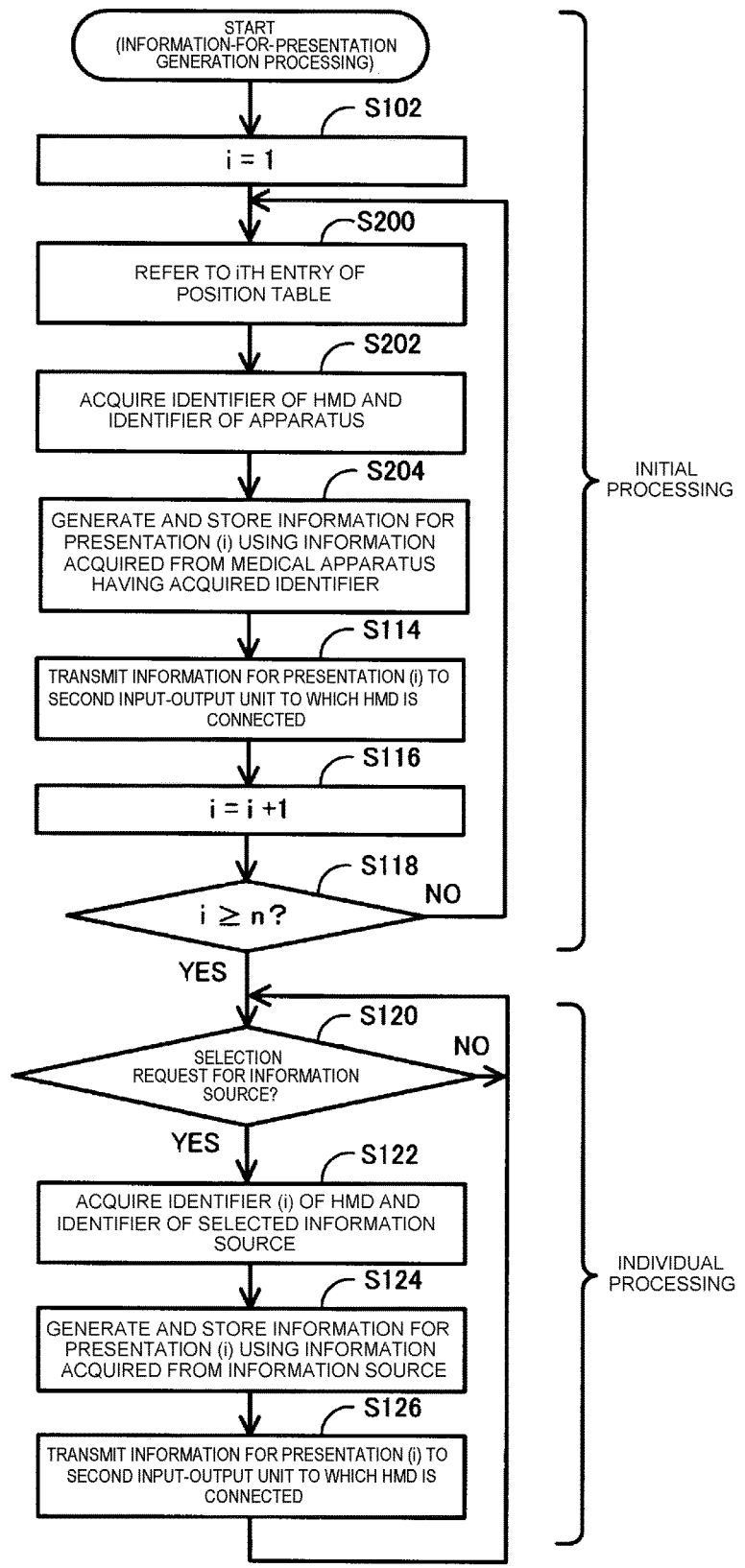

[Fig. 19A]
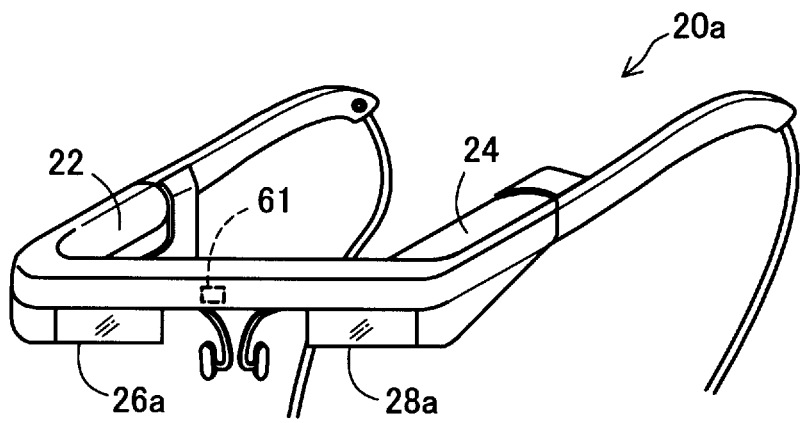
[Fig. 19B]
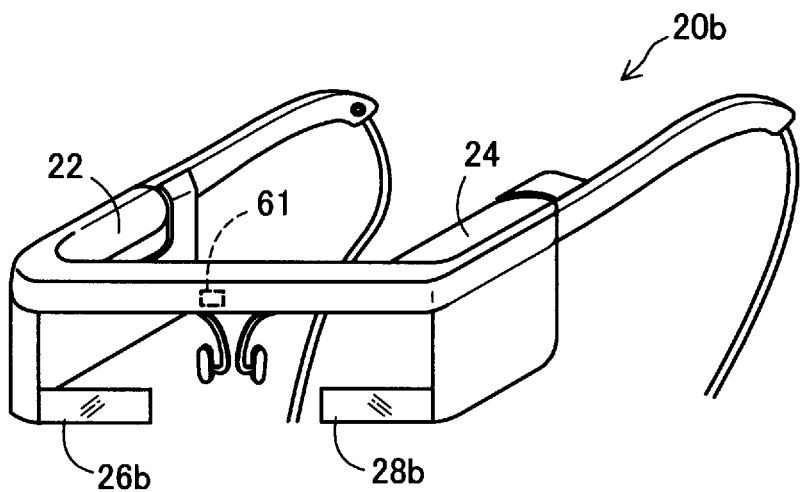

INFORMATION PROCESSING APPARATUS, INFORMATION PROCESSING METHOD, AND INFORMATION PROCESSING SYSTEM

TECHNICAL FIELD

The present invention relates to an information processing apparatus.

BACKGROUND ART

There is known a head mounted display apparatus (a head mounted display (HMD)), which is a display apparatus mounted on the head. For example, the head mounted display apparatus generates, using a liquid crystal display and a light source, image light representing an image and leads the generated image light to the eyes of a user using a projection optical system, a light guide plate, and the like to thereby cause the user to recognize a virtual image.

PTL 1 describes a system for improving display of information in a medical environment using such a head mounted display apparatus. In the technique described in PTL 1, information is acquired from a plurality of information sources on the basis of a query. The acquired information is subjected to filter processing on the basis of rules and projected on eyepieces of an eyeglass headset-type viewer. In the technique described in PTL 1, a control right and a priority right concerning display of a fixed large display are determined on the basis of the visual line of a wearer of the head mounted display apparatus. PTL 2 describes a face mounted video display apparatus for medical use (a head mounted display apparatus). In the technique described in PTL 2, operation state information of endoscope peripheral devices used together with an endoscope during an endoscopic examination or an endoscopic surgery is displayed on the head mounted display apparatus. PTL 3 and 4 describes a method for performing display of information in a dental surgery by applying an augmented reality technique in the head mounted display apparatus. In the technique described in PTL 3 and PTL 4, a preoperative image, a simulation image, and the like are displayed to be superimposed on an actual image of a site of operation.

CITATION LIST

Patent Literature

[PTL 1]
JP-A-2006-102495
[PTL 2]
JP-A-2001-104331
[PTL 3]
JP-A-2010-259497
[PTL 4]
JP-A-2013-34764

SUMMARY OF INVENTION

Technical Problem

According to the progress of medicine and the progress of electronic devices, the present medical sites have made rapid progress. In the medical sites, a variety of apparatuses for medical use (hereinafter referred to as "medical apparatuses") such as an electrocardiogram, a heart rate meter, a blood pressure meter, a pulse oximeter, a blood sugar value meter, an X-ray, and an endoscope are used. It is a great burden for those engaged in the medical sites to grasp information concerning the variety of medical apparatuses and perform work. Therefore, there has been a demand for a system that can unify the information concerning the variety of medical apparatuses. In the technique described in PTL 1, although it is possible to acquire information from a plurality of information sources (medical apparatuses), there is a problem in that setting of a query and a filter is difficult. In the techniques described in PTL 2 to PTL 4, since medical apparatuses applied with the techniques are limited, there is a problem in that the information concerning the variety of medical apparatuses cannot be unified.

Such problems are not limited to the head mounted display apparatus and are common to all information processing apparatuses that generate information to be displayed on an image display apparatus such as the head mounted display apparatus. Therefore, there is a demand for an information processing apparatus capable of unifying the information concerning the variety of medical apparatuses and capable of easily filtering information from the unified information and generating information to be displayed on the image display apparatus. Besides, concerning the information processing apparatus, there have been various demands such as improvement of versatility, improvement of convenience, a reduction in manufacturing costs, and improvement of reliability.

Solution to Problem

An advantage of some aspects of the invention is to solve at least apart of the problems described above, and the invention can be implemented as the following forms.

(1) An aspect of the invention provides an information processing apparatus. The information processing apparatus includes: an acquiring unit that acquires a plurality of kinds of medical apparatus information, which are information acquired from a plurality of medical apparatuses; a generating unit that generates information for presentation including at least a part of the plurality of kinds of medical apparatus information acquired by the acquiring unit; and a presenting unit that outputs the generated information for presentation to an image display apparatus that displays an image. The generating unit generates the information for presentation including at least the medical apparatus information acquired by the medical apparatus, visual recognition of a display unit of which by a user of the image display apparatus is difficult. With the information processing apparatus according to this aspect, since the generating unit generates the information for presentation including at least one of the plurality of kinds of medical apparatus information acquired by the acquiring unit, it is possible to unify information concerning a variety of medical apparatuses (medical apparatus information) connected to the information processing apparatus. Since the generating unit generates the information for presentation including at least the medical apparatus information acquired by the medical apparatus, the visual recognition of the display unit of which by the user of the image display apparatus is difficult, it is possible to extract information from the unified medical apparatus information under a condition that information is the medical apparatus information acquired by the medical apparatus, the visual recognition of the display unit of which by the user of the image display apparatus is difficult, and include the extracted information in the information for presentation. As a result, it is possible to realize the information processing apparatus capable of unifying the information concerning the variety of medical apparatuses and capable of easily filtering information from the unified information and generating information to be displayed on the image display apparatus.

(2) The information processing apparatus according to the aspect described above may be configured such that the presenting unit further acquires an image in a visual field direction of the user of the image display apparatus, and the information processing apparatus further includes a specifying unit that performs image recognition of the acquired image in the visual field direction, specifies the medical apparatus, the display unit of which is not included in the image in the visual field direction, and specifies the specified medical apparatus as the medical apparatus, the visual recognition of which is difficult. With the information processing apparatus according to this aspect, the specifying unit can specify, on the basis of the image in the visual field direction of the user of the image display apparatus, the medical apparatus, the visual recognition of the display unit of which by the user is difficult. The specifying unit can acquire information necessary in specifying the medical apparatus via the presenting unit. This is convenient because the user does not need to prepare data and the like in advance in using the information processing apparatus.

(3) The information processing apparatus according to the aspect described above may be configured such that the acquiring unit further respectively acquires position information of the plurality of medical apparatuses connected to the information processing apparatus, the presenting unit further acquires present position information representing a present position of the image display apparatus connected to the information processing apparatus and direction information representing a direction of the head of the user, and the information processing apparatus further includes a specifying unit that specifies the medical apparatus, the visual recognition of which is difficult, using the position information of the plurality of medical apparatuses acquired by the acquiring unit and the present position information and the direction information of the image display apparatus acquired by the presenting unit. With the information processing apparatus according to this aspect, the specifying unit can automatically specify the medical apparatus, the visual recognition of the display unit of which by the user of the image display apparatus is difficult, using the position information of the plurality of medical apparatuses acquired by the acquiring unit and the present position information and the direction information of the image display apparatus acquired by the presenting unit. The specifying unit can acquire information necessary in specifying the medical apparatus via the acquiring unit and the presenting unit. This is convenient because the user does not need to prepare data and the like in advance in using the information processing apparatus.

(4) The information processing apparatus according to the aspect described above may be configured such that the information processing apparatus further includes: an arrangement storing unit that stores information for specifying the medical apparatus, the visual recognition of which is difficult; and a specifying unit that specifies the medical apparatus, the visual recognition of which is difficult, using the arrangement storing unit. With the information processing apparatus according to this aspect, the specifying unit can automatically specify the medical apparatus, the visual recognition of the display unit of which by the user of the image display apparatus is difficult, using the arrangement storing unit that stores the information for specifying the medical apparatus, the visual recognition of the display unit of which by the user of the image display apparatus is difficult. The specifying unit can acquire information necessary in specifying the medical apparatus from the arrangement storing unit prepared in advance. Therefore, even when the medical apparatus and the image display apparatus connected to the information processing apparatus do not include detecting means for position information and acquiring means for an outside scene image, the specifying unit can automatically specify the medical apparatus, the visual recognition of the display unit of which by the user of the image display apparatus is difficult.

(5) The information processing apparatus according to the aspect described above may be configured such that the information processing apparatus further includes an invisible-information storing unit that stores invisible information, which is information not appearing in an external appearance of an object, and the generating unit includes the invisible information in the information for presentation to be generated. With the information processing apparatus according to this aspect, since the information processing apparatus includes the invisible-information storing unit, it is possible to unify the invisible information stored in the invisible-information storing unit in addition to the medical apparatus information of the variety of medical apparatuses connected to the information processing apparatus. The generating unit extracts, from the unified information, the invisible information, which is the information not appearing in the external appearance of the object, such as a CT image, an MRI image, a X-ray image, a transparent image, an ultrasonic diagnosis image, an endoscope image, or a thermography image and generates the information for presentation to be displayed on the image display apparatus. As a result, the user of the image display apparatus connected to the information processing apparatus can visually recognize the invisible information. This leads to improvement of convenience of the image display apparatus.

(6) The information processing apparatus according to the aspect described above may be configured such that at least one medical apparatus for acquiring invisible information, which is information not appearing in an external appearance of an object, is connected to the information processing apparatus, and the generating unit includes, in the information for presentation to be generated, the medical apparatus information acquired by the medical apparatus for acquiring the invisible information. With the information processing apparatus according to this aspect, the generating unit extracts the medical apparatus information acquired by the medical apparatus for acquiring the invisible information, which is the information not appearing in the external appearance of the object, such as a CT image, an MRI image, a X-ray image, a transparent image, an ultrasonic diagnosis image, an endoscope image, or a thermography image and generates the information for presentation to be displayed on the image display apparatus. As a result, the user of the image display apparatus connected to the information processing apparatus can visually recognize the invisible information. This leads to improvement of convenience of the image display apparatus.

(7) The information processing apparatus according to the aspect described above may be configured such that at least one medical apparatus for acquiring an image of treatment of a patient is connected to the information processing apparatus, and the generating unit includes, in the information for presentation to be generated, the medical apparatus information acquired by the medical apparatus for acquiring the image of the treatment. With the information processing apparatus according to this aspect, the generating unit extracts the medical apparatus information acquired by the medical apparatus for acquiring the image of the treatment of the patient and generates the information for presentation to be displayed on the image display apparatus. As a result, the user of the image display apparatus connected to the information processing apparatus can visually recognize the image of the treatment of the patient. This leads to improvement of convenience of the image display apparatus.

(8) The information processing apparatus according to the aspect described above may be configured such that the generating unit enlarges or reduces, in generating the information for presentation, an image included in the medical apparatus information while maintaining an aspect ratio of the image. With the information processing apparatus according to this aspect, the generating unit enlarges or reduces the image included in the medical apparatus information while maintaining the aspect ratio of the image. Therefore, when the information for presentation is generated, it is possible to suppress an unexpected distortion from occurring in the medical apparatus information acquired by the medical apparatus.

(9) The information processing apparatus according to the aspect described above may be configured such that a head mounted display apparatus, with which the user can simultaneously visually recognize a virtual image and an outside scene, is connected to the information processing apparatus as the image display apparatus. With the information processing apparatus according to this aspect, it is possible to realize the information processing apparatus capable of unifying the information concerning the variety of medical apparatuses and capable of easily filtering information from the unified information and generating information to be displayed on the head mounted display apparatus of a so-called transmission type.

(10) The information processing apparatus according to the aspect described above may be configured such that the presenting unit further acquires, from the head mounted display apparatus, an image in a visual field direction of the user in a state in which the head mounted display apparatus is worn, performs image recognition of the acquired image in the visual field direction to extract a characteristic of an object included in the outside scene, corrects, on the basis of the extracted characteristic, the information for presentation generated by the generating unit, and outputs the information for presentation after the correction. With the information processing apparatus according to this aspect, the presenting unit performs the image recognition of the image in the visual field direction of the user of the head mounted display apparatus to extract the characteristic of the object included in the outside scene and corrects the generated information for presentation on the basis of the extracted characteristic. Therefore, when invisible information such as a CT image, an MRI image, or an X-ray image is included in the information for presentation, it is possible to match the invisible information to the object (for example, a body of a patient) included in the outside scene. As a result, it is possible to improve convenience of the user of the head mounted display apparatus. Further, the head mounted display apparatus can receive the information for presentation after the correction. Therefore, the head mounted display apparatus only has to directly display the received information for presentation. As a result, it is possible to simplify the configuration of the head mounted display apparatus.

(11) Another aspect of the invention provides an information processing system. The information processing system includes: a plurality of medical apparatuses; an information processing apparatus; and a head mounted display apparatus with which a user can simultaneously visually recognize a virtual image and an outside scene. The information processing apparatus includes: an acquiring unit that acquires a plurality of kinds of medical apparatus information, which are information acquired from the plurality of medical apparatuses; a generating unit that generates information for presentation including at least apart of the plurality of kinds of medical apparatus information acquired by the acquiring unit; and a presenting unit that outputs the generated information for presentation to the head mounted display apparatus. The head mounted display apparatus includes: an information-for-presentation acquiring unit that acquires the information for presentation from the information processing apparatus; and an image display unit that causes the user of the head mounted display apparatus to visually recognize the acquired information for presentation as the virtual image. The generating unit of the information processing apparatus generates the information for presentation including at least the medical apparatus information acquired by the medical apparatus, visual recognition of a display unit of which by the user of the head mounted display apparatus is difficult. With the information processing system according to this aspect, it is possible to realize the information processing system capable of unifying information concerning a variety of medical apparatuses (medical apparatus information) and capable of easily filtering information from the unified information, generating the information for presentation, and causing the user of the head mounted display apparatus of a so-called transmission type to visually recognize the generated information for presentation as a virtual image.

(12) Still another aspect of the invention provides a head mounted display apparatus that is connected to the information processing apparatus according to the aspect explained above and with which a user can simultaneously visually recognize a virtual image and an outside scene. The head mounted display apparatus includes: an image acquiring unit that acquires an image in a visual field direction of the user in a state in which the head mounted display apparatus is worn; a specifying unit that performs image recognition of the acquired image in the visual field direction, specifies the medical apparatus, the display unit of which is not included in the image in the visual field direction, and specifies the specified medical apparatus as the medical apparatus, the visual recognition of which is difficult; a notifying unit that notifies the information processing apparatus of the specified medical apparatus; an information-for-presentation acquiring unit that acquires the information for presentation from the information processing apparatus; and an image display unit that causes the user to visually recognize the acquired information for presentation as the virtual image. With the head mounted display apparatus according to this aspect, the specifying unit can be provided in the head mounted display apparatus. As a result, it is possible to reduce a processing load in the information processing apparatus.

Not all of the components included in the aspects of the invention explained above are essential. To solve a part or all of the problems or attain a part or all of the effects described in this specification, it is possible to perform change, deletion, replacement with new components, and partial deletion of limited contents as appropriate concerning a part of the plurality of components. To solve a part or all of the problems or attain a part or all of the effects described in this specification, it is also possible to combine a part or all of the technical features included in an aspect of the invention with apart of all of the technical features included in the other aspects of the invention to obtain an independent aspect of the invention.

For example, an aspect of the invention can be realized as an apparatus including apart or all of the three components, i.e., the acquiring unit, the generating unit, and the presenting unit. That is, this apparatus may include or may not include the acquiring unit. This apparatus may include or may not include the generating unit. This apparatus may include or may not include the presenting unit. Such an apparatus can be realized as, for example, an information processing apparatus. However, the apparatus can also be realized as apparatuses other than the information processing apparatus. A part or all of the technical features of the aspects of the information processing apparatus can be applied to this apparatus.

Note that the invention can be realized in various forms. For example, the invention can be realized in forms of an information processing apparatus, an information processing method, an information processing system, a head mounted display apparatus, a control method for the head mounted display apparatus, a head mounted display system, a computer program for realizing functions of the methods, the apparatuses, or the systems, a recording medium having the computer program recorded therein, and the like.

BRIEF DESCRIPTION OF DRAWINGS

FIG. 1 is an explanatory diagram showing the schematic configuration of an information processing system in an embodiment of the invention.

FIG. 2 is a block diagram functionally showing the configuration of an information processing apparatus.

FIG. 3 is an explanatory diagram showing an example of a common video specification.

FIG. 4 is an explanatory diagram showing an example of a management table.

FIG. 5 is a block diagram functionally showing the configuration of a head mounted display.

FIG. 6 is a flowchart for explaining a procedure of information-for-presentation generation processing.

FIG. 7 is an explanatory diagram showing an example of the arrangement of medical apparatuses and the head mounted display.

FIG. 8 is an explanatory diagram for explaining a method of specifying a medical apparatus, visual recognition of a display unit of which by a user of the head mounted display is difficult.

FIG. 9A is an explanatory diagram for explaining a method of generating information for presentation.

FIG. 9B is an explanatory diagram for explaining a method of generating information for presentation.

FIG. 10 is an explanatory diagram for explaining a method of generating information for presentation.

FIG. 11 is an explanatory diagram showing a state in which the information for presentation is displayed as a virtual image on the head mounted display.

FIG. 12 is an explanatory diagram showing a state in which the information for presentation is displayed as virtual images in a plurality of head mounted displays present in different places.

FIG. 13A is an explanatory diagram showing a first example of the information for presentation.

FIG. 13B is an explanatory diagram showing a first example of the information for presentation.

FIG. 14A is an explanatory diagram showing a second example of the information for presentation.

FIG. 14B is an explanatory diagram showing a second example of the information for presentation.

FIG. 15 is an explanatory diagram showing a third example of the information for presentation.

FIG. 16 is a block diagram functionally showing the configuration of an information processing apparatus in a second embodiment.

FIG. 17 is an explanatory diagram showing an example of a position table.

FIG. 18 is a flowchart for explaining a procedure of information-for-presentation generation processing in the second embodiment.

FIG. 19A is an explanatory diagram showing the configuration of an external appearance of a head mounted display in a modification.

FIG. 19B is an explanatory diagram showing the configuration of an external appearance of a head mounted display in a modification.

DESCRIPTION OF EMBODIMENTS

A. First Embodiment

A-1. Configuration of an Information Processing System

FIG. 1 is an explanatory diagram showing the schematic configuration of an information processing system 1000 in an embodiment of the invention. The information processing system 1000 includes a plurality of medical apparatuses 501 to 50$n$, an information processing apparatus 300, and an image display apparatus 100. The information processing system 1000 is a system used in a medical site. The information processing apparatus 300 acquires information from the plurality of medical apparatuses 501 to 50$n$, unifies the information, and generates information for presentation to be displayed on the image display apparatus 100. The medical apparatuses 501 to 50$n$ and the image display apparatus 100 are connected to the information processing apparatus 300 by wire or by radio. Note that, in the following explanation, as a character indicating an "arbitrary plural", "n" is used. n is an integer equal to or larger than 1.

In this embodiment, an operation site in an operation room is illustrated as a medical site. However, the information processing system 1000 may be used in a diagnosis room, an operational room, a treatment room, a delivery room, and the like. In this embodiment, a head mounted display apparatus is illustrated as the image processing apparatus 100. However, the image display apparatus 100 may be a stationary display, a portable display, a smart phone, and the like. In the following explanation, the head mounted display apparatus 100 is also referred to as "head mounted display (HMD)". In FIG. 1, one head mounted display 100 is shown. However, as shown in FIG. 2 referred to below, a plurality of head mounted displays 100$a$ to 100$n$ may be connected to the information processing apparatus 300.

Note that, in the following explanation, when the head mounted displays 100$a$ to 100$n$ are explained without being particularly distinguished, the head mounted displays 100$a$ to 100$n$ are simply referred to as "head mounted display 100". Similarly, when the medical apparatuses 501 to 50$n$ are explained without being particularly distinguished, the medical apparatuses 501 to 50$n$ are simply referred to as "medical apparatus(es) 500".

The medical apparatuses 501 to 50$n$ are various apparatuses used in a medical use. As examples of the medical apparatuses 501 to 50$n$, for example, a visible light camera for photographing a still image and a moving image inside and outside a room, a visible light camera for photographing a still image and a moving image of a site of operation, an electrocardiogram examination apparatus, a timer for surgery, a biological monitor, a heart rate meter, a pulse rate meter, a blood pressure meter, an ultrasonic examination apparatus, a pulse oximeter, a blood sugar value meter, a CT (Computer tomography) image photographing apparatus, an MRI (Magnetic Resonance Imaging) image photographing apparatus, an X-ray image photographing apparatus, a transparent image photographing apparatus, an endoscope image photographing apparatus, a thermography image photographing apparatus can be used.

A-2. Configuration of the Information Processing Apparatus

FIG. 2 is a block diagram functionally showing the configuration of the information processing apparatus 300. The information processing apparatus 300 includes a first input-output unit 310, a ROM 320, a RAM 330, a communication interface 340, a CPU 350, and an external storage device 380. The units are connected to one another by a bus.

The first input-output unit 310 functioning as an acquiring unit includes a plurality of first input-output units 311 to 31n. The first input-output units 311 to 31n are input-output interfaces conforming to a communication standard such as a USB (Universal Serial Bus), an HDMI (High Definition Multimedia Interface (registered trademark)), a DVI (Digital Visual Interface), a VGA (Video Graphics Array), a composite, an RS-232C (Recommended Standard 232), an infrared ray, short-range radio communication (e.g., Bluetooth (registered trademark)), a wireless LAN (e.g., IEEE802.11), and a wired LAN (e.g., IEEE802.3). The first input-output units 311 to 31n respectively acquire information input from the medical apparatuses 501 to 50n connected thereto. The information input from the medical apparatuses is information, for example, measured or picked up by the medical apparatuses. In the following explanation, the information is also referred to as "medical apparatus information".

In this embodiment, the first input-output unit 311 is an input-output interface conforming to the DVI. The first input-output unit 312 is an input-output interface conforming to the HDMI. The first input-output unit 313 is an input-output interface conforming to the HDMI. The first input-output unit 31n is an input-output interface conforming to the radio LAN. In FIG. 2, the medical apparatus 501 and a stationary display 700 are connected to the first input-output unit 311. Similarly, the medical apparatus 502 is connected to the first input-output unit 312. The medical apparatus 503 is connected to the first input-output unit 313. The medical apparatus 50n is connected to the first input-output unit 31n. In this way, the first input-output unit 310 is configured by the first input-output units 311 to 31n conforming to the different kinds of communication standards. Therefore, it is possible to connect medical apparatuses conforming to various communication standards to the first input-output unit 310. It is possible to improve versatility of the information processing apparatus 300. Note that the first input-output unit 310 can also directly output an input signal to a display apparatus such as the display 700.

The communication interface (I/F) 340 is an interface of the wired LAN. The communication interface 340 communicably connects a doctor PR in an external facility and the information processing apparatus 300 through a line such as the Internet INT and communicably connects a database OD connected to an in-hospital LAN and the information processing apparatus 300 through an intranet. The doctor PR is assumed to be, for example, a doctor who supervises a user of the head mounted display 100 connected to the information processing apparatus 300, an outside expert, or the like. In the database OD, procedure information representing procedures of treatment such as an operation, an electronic clinical record system, electronic academic books, and the like are stored.

The CPU 350 expands a computer program stored in the ROM 320 on the RAM 330 and executes the computer program to thereby control the information processing apparatus 300. The CPU 350 realizes functions of a generating unit 360 and a second input-output unit 370. The generating unit 360 executes information-for-presentation generation processing explained below to generate information for presentation to be displayed on the head mounted display 100. The generating unit 360 in this embodiment generates information for presentation including medical apparatus information of the medical apparatus 500, visual recognition of a display unit of which by the user of the head mounted display 100 is difficult. The generating unit 360 includes a specifying unit 361. The specifying unit 361 specifies the medical apparatus 500, the visual recognition of the display unit of which by the user of the head mounted display 100 is difficult. "The medical apparatus 500, the visual recognition of the display unit of which by the user is difficult" is, for example, a general term of the medical apparatus 500 explained below.

Since the medical apparatus 500 is present at a dead angle of the user, the user cannot or cannot easily visually recognize the display unit (a display, etc.) of the medical apparatus 500.

Since the medical apparatus 500 is present in a place away from the user, the user cannot or cannot easily visually recognize the display unit of the medical apparatus 500.

Although the medical apparatus 500 is not present at the dead angle of the user and is present in a place near from the user, since a visual line of the user and the display unit are not opposed to each other, the user cannot or cannot easily visually recognize the display unit of the medical apparatus 500.

The second input-output unit 370 functioning as a presenting unit includes a plurality of second input-output units 371 to 37n. Like the first input-output unit 310, the second input-output units 371 to 37n are input-output interfaces conforming to various communication standards. Since details are the same as the details of the first input-output unit 310, explanation of the details is omitted.

In this embodiment, the second input-output unit 371 and the second input-output unit 372 are input-output interfaces conforming to the wireless LAN. The second input-output unit 373 is an input-output interface conforming to the USB. The second input-output unit 37n is an input-output interface conforming to the DVI. In FIG. 2, the head mounted display 100a functioning as an image display apparatus is connected to the second input-output unit 371. Similarly, the head mounted display 100b is connected to the second input-output unit 372. The head mounted display 100c is connected to the second input-output unit 373. The head mounted display 100n is connected to the second input-output unit 37n. In this way, the second input-output unit 370 is configured to the second input-output units 371 to 37n conforming to the different kinds of communication standards. Therefore, it is possible to connect head mounted display conforming to various communication standards to the second input-output unit 370. It is possible to improve versatility of the information processing apparatus 300.

The external storage device 380 is configured by a ROM, a RAM, a DRAM, a hard disk, a flash memory, and the like not shown in the figure. The external storage device 380 includes a common video specification 381, a management table 382, invisible information 383 functioning as an invisible-information storing unit, and a record of operation 384.

FIG. 3 is an explanatory diagram showing an example of the common video specification 381. The common video specification 381 is a table for specifying standard specifications concerning a video signal of information for presentation. The common video specification 381 is used when the generating unit 360 generates the information for presentation in the information-for-presentation generation processing.

In the common video specification 381 in this embodiment, the number of pixels, an aspect ratio, the resolution, a compression method, and an encoding method of an image included in the video signal are included as specifications of the video signal. The common video specification 381 is determined in advance and stored in the external storage device 380. When the common video specification 381 is determined, it is preferable to take into account specifications of the video signal adopted in the head mounted displays 100a to 100n connected to the second input-output unit 370.

FIG. 4 is an explanatory diagram showing an example of the management table 382. The management table 382 is a table for managing information concerning the head mounted display 100 connected to the second input-output unit 370 and, more specifically, for managing information concerning the head mounted displays 100a to 100n respectively connected to the second input-output units 371 to 37n. The management table 382 is used when the generating unit 360 generates the information for presentation in the information-for-presentation generation processing and is also used when the second input-output units 371 to 37n transmit the information for presentation to the head mounted displays 100a to 100n.

In the management table 382 in this embodiment, an identifier, a role, and a video specification are stored in association with one another. In the "identifier", unique identifiers for identifying the head mounted displays 100 connected to the second input-output unit 370 from one another are stored. In the "role", character strings representing what kinds of roles users of the head mounted displays 100 identified by the identifiers play in a medical site are stored. In the "video specification", character strings representing patterns of specifications of the video signal (the number of pixels, an aspect ratio, the resolution, a compression method, an encoding method, and the like of an image included in the video signal) in the head mounted displays 100 identified by the identifiers are stored.

In the example shown in FIG. 4, it is seen that a user of the head mounted display 100 identified by an identifier "1" is an "operating surgeon" and the video specification of the head mounted display 100 is a "specification A" (an entry E01). Similarly, it is seen that a user of the head mounted display 100 identified by an identifier "n" is a "nurse" and the video specification of the head mounted display 100 is a "specification E" (an entry E0n).

The management table 382 may be determined in advance and stored in the external storage device 380 or may be automatically generated in initial processing when the head mounted display 100 is connected to the information processing apparatus 300. Specifically, for example, when the generating unit 360 detects the connection of the head mounted display 100 to the second input-output unit 370, the generating unit 360 gives a unique identifier to the head mounted display 100 and acquires a role of the user and a video specification from the head mounted display 100. The generating unit 360 stores the given identifier and the acquired role and the acquired video specification in the management table 382. By performing the initial processing every time the head mounted displays 100a to 100n are connected to the second input-output unit 370, the generating unit 360 can automatically generate the management table 382.

Invisible information, which is information not appearing in an external appearance of an object, is stored in the invisible information 383 (the invisible-information storing unit) shown in FIG. 2. The invisible information is image or character information representing the structure of the object. When the object is an organism, the invisible information is, for example, a CT image, an MRI image, an X-ray image, a transparent image, an ultrasonic diagnosis image, an endoscope image, a thermography image, and character information incidental to the images. The invisible information is photographed in advance and stored in the invisible information 383.

The record of operation 384 shown in FIG. 2 is a recording unit for recording the medical apparatus information acquired by the information processing apparatus 300, the information for presentation generated by the information processing apparatus 300, and data and time of the acquisition or the generation in association with one another. The medical apparatus information acquired by the information processing apparatus 300 means medical apparatus information acquired by the information processing apparatus 300 from the plurality of medical apparatuses 501 to 50n respectively connected to the first input-output units 311 to 31n. The information for presentation generated by the information processing apparatus 300 means all kinds of information for presentation generated by the generating unit 360 in the information-for-presentation generation processing. The record of the information acquired and generated by the information processing apparatus 300 can be regarded substantially the same as a log of an operation (diagnosis, treatment, and curing). Consequently, after the operation or the like ends, it is possible to use the log of the operation for an analysis of operation content, training, learning scholarship, and the like.

A-3. Configuration of the Mounted Display Apparatus

FIG. 5 is a block diagram functionally showing the configuration of the head mounted display 100a. In the following explanation, the head mounted display 100a is illustrated and explained as an example of the configuration of the head mounted display 100. The head mounted display 100a is a head mounted display apparatus of an optical transmission type with which the user can visually recognize a virtual image and, at the same time, directly visually recognize an outside scene. The head mounted display 100a displays, as a virtual image, information for presentation received from the information processing apparatus 300. The head mounted display 100a includes an image display unit 20 that causes the user to visually recognize the virtual image in a state in which the head mounted display 100a is mounted on the head of the user and a control unit 10 that controls the image display unit 20. The image display unit 20 and the control unit 10 perform transmission of various signals via a cable 40.

A-3-1. Configuration of the Control Unit

The control unit 10 includes an input-information acquiring unit 110 that acquires an operation input to an input device such as a touch pad, a cross key, a foot switch, a gesture, or a microphone, a storing unit 120 configured by a ROM, a hard disk, or the like, a power supply 130 that supplies electric power to the units of the head mounted display 100a, a radio communication unit 132 that performs radio communication with other apparatuses according to a predetermined radio communication standard such as the wireless LAN, Bluetooth, or the like, a present-position acquiring unit 134, a CPU 140, an interface 180 for connecting the information processing apparatus 300 and various external apparatuses OA, and transmitting units (Tx) 51 and 52. The units are connected to one another by a not-shown bus. The present-position acquiring unit 134 receives a signal from a GPS satellite to thereby detect a present position of a user of the head mounted display 100a and generates present position information representing the present position of the user. Note that the present-position acquiring unit 134 may receive radio waves of a plurality of base stations and determine strength of the received radio waves to thereby generate the present position information. The present position information can be realized by, for example, a coordinate representing latitude and longitude. Like the first input-output unit 310 of the information processing apparatus 300, the interface 180 can conform to various communication standards.

The CPU 140 reads out and executes a computer program stored in the storing unit 120 to thereby function as an operating system (OS) 150, an image processing unit 160, a sound processing unit 170 that supplies sound signals to a speaker of a right earphone 32 and a speaker of a left earphone 34, and a display control unit 190. The image processing unit 160 generates a signal on the basis of a video signal of information for presentation input via the interface 180 functioning as an information-for-presentation acquiring unit or the radio communication unit 132. The image processing unit 160 supplies the generated signal to the image display unit 20 via the transmitting units 51 and 52 and the cable 40 to thereby control display on the image display unit 20. As the signal supplied to the image display unit 20, a well-known analog format or a digital format can be used. The display control unit 190 generates a control signal for controlling a right display driving unit 22 and a left display driving unit 24 of the image display unit 20 and transmits the control signal via the transmitting units 51 and 52. The control signal is a signal for individually switching driving ON/OFF of a right LCD 241 by a right LCD control unit 211, driving ON/OFF of a right backlight 221 by a right backlight control unit 201, driving ON/OFF of a left LCD 242 by a left LCD control unit 212, and driving ON/OFF of a left backlight 222 by a left backlight control unit 202.

A-3-2. Configuration of the Image Display Unit

The image display unit 20 is a wearing body worn on the head of the user. In this embodiment, the image display unit 20 has an eyeglass shape. The image display unit 20 includes the right display driving unit 22 and the left display driving unit 24 that generate and emit image light representing an image, a right optical-image display unit 26 and a left optical-image display unit 28 (FIG. 2) that guide the image light to both the eyes of the user, a camera 61 functioning as an image acquiring unit, and a 9-axis sensor 66.

The right display driving unit 22 includes a receiving unit (Rx) 53, the right backlight (BL) control unit 201 and the right backlight (BL) 221 functioning as a light source, the right LCD (Liquid Crystal Display) control unit 211 and the right LCD 241 functioning as a display element, and a right projection optical system 251. The right backlight control unit 201 drives the right backlight 221 on the basis of a control signal input via the receiving unit 53. The right backlight 221 is, for example, a light emitting body such as an LED or an electroluminescence (EL). The right LCD control unit 211 drives the right LCD 241 on the basis of an input video signal. The right LCD 241 is a transmissive liquid crystal panel in which a plurality of pixels are arranged in a matrix shape. The right LCD 241 drives liquid crystal in pixel positions arranged in the matrix shape to change the transmittance of light transmitted through the right LCD 241 and modulates illumination light irradiated from the right backlight 221 into effective image light representing an image. The right projection optical system 251 is configured by a collimate lens that changes the image light emitted from the right LC 241 to light beams in a parallel state. The left display driving unit 24 includes a configuration same as the right display driving unit 22 and operates in the same manner as the right display driving unit 22.

The right optical-image display unit 26 and the left optical-image display unit 28 are arranged to be located in front of the left and right eyes of the user when the user wears the image display unit 20 (FIG. 2). The right optical-image display unit 26 includes a right light guide plate 261 formed of a light transmissive resin material or the like. The right light guide plate 261 guides image light output from the right display driving unit 22 to a right eye RE of the user while reflecting the image light along a predetermined optical path. In the right guide plate 261, a diffraction grating may be used or a semi-transmissive reflection film may be used. The left optical-image display unit 28 includes a configuration same as the right optical-image display unit 26 and operates in the same manner as the right optical-image display unit 26. In this way, the image light guided to both the eyes of the user of the head mounted display 100a is focused on the retinas of the user, whereby the user can visually recognize a virtual image. The user of the head mounted display 100a in this embodiment can simultaneously view the virtual image and an outside scene behind the virtual image in a portion where the virtual image is displayed in a visual field. In a portion where the virtual image is not displayed in the visual field, the user can directly view the outside scene through the left and right optical-image display units 26 and 28.

The 9-axis sensor 66 is a motion sensor that detects acceleration (3 axes), angular velocity (3 axes), and terrestrial magnetism (3 axes). When the image display unit 20 is worn on the head of the user, the 9-axis sensor 66 functions as a movement detecting unit that detects the movement of the head of the user of the head mounted display 100a. The movement of the head includes the speed, the acceleration, the angular velocity, the direction, and a change in the direction of the head. Note that the direction of the head is also referred to as "direction information". The camera 61 functioning as a visual-field-image acquiring unit is arranged in a position corresponding to the middle of the forehead of the user when the user wears the image display unit 20. The camera 61 picks up an outside scene (a view on the outside) in a front side direction of the image display unit 20, in other words, a visual field direction of the user in a state in which the head mounted display 100a is mounted and acquires an outside scene image. The camera 61 is a so-called visible light camera. The camera 61 in this embodiment is a monocular camera. However, a stereo camera may be adopted.

A-4. Information-for-Presentation Generation Processing

FIG. 6 is a flowchart for explaining a procedure of the information-for-presentation generation processing. The information-for-presentation generation processing is processing for generating information for presentation to be displayed on the head mounted display 100. The generating unit 360 of the information processing apparatus 300 (FIG. 2) executes the information-for-presentation generation processing. The information-for-presentation generation processing can be roughly divided into initial processing including steps S100 to S118 and individual processing including steps S120 to S126.

A-4-1. Initial Processing

In the initial processing, the generating unit 360 automatically specifies the medical apparatus 500, visual recognition of the display unit of which by the user of the head mounted display 100 is difficult, and generates information for presentation including medical apparatus information acquired from the specified medical apparatus 500.

FIG. 7 is an explanatory diagram showing an example of the arrangement of the medical apparatus 500 and the head mounted display 100. In step S100 of the information-for-presentation generation processing (FIG. 6), the specifying unit 361 of the generating unit 360 acquires position information of all the medical apparatuses 500 connected to the information processing apparatus 300 and present position information of all the head mounted displays 100 and causes the ROM 320 (or the external storage device 380) to store the position information and the present position information. Specifically, the specifying unit 361 requests the medical apparatuses 501 to 50n to transmit position information. The specifying unit 361 causes the ROM 320 to store position information representing positions MP1 to MPn (FIG. 7) of the medical apparatuses 501 to 50n received together with responses. Similarly, the specifying unit 361 requests the head mounted displays 100a to 100n to transmit present position information. The specifying unit 361 causes the ROM 320 to store present position information representing present positions UP1 to UPn (FIG. 7) of the head mounted display 100a to 100n received together with responses.

In step S102 of the information-for-presentation generation processing (FIG. 6), the generating unit 360 sets "1" in a variable i in the information-for-presentation generation processing. Thereafter, the specifying unit 361 of the generating unit 360 refers to an ith entry of the management table 382 (step S104). The specifying unit 361 of the generating unit 360 acquires an "identifier" of the head mounted display 100 stored in the ith entry of the management table 382 (step S106).

Note that, in the following explanation, the head mounted display 100 having the identifier acquired in step S106 is also referred to as "head mounted display 100i". The head mounted display 100i indicates the head mounted display 100 that is currently performing processing in the initial processing. For example, when the variable i is 1, the head mounted display 100i indicates a head mounted display 100a of the operating surgeon, the identifier of which is 1, stored in the first entry E01 of the management table 382.

In step S108 of the information-for-presentation generation processing (FIG. 6), the specifying unit 361 of the generating unit 360 requests the head mounted display 100i to transmit present position information and direction information and acquires present position information and direction information of the head mounted display 100i received together with a response. Thereafter, the specifying unit 361 of the generating unit 360 specifies, using the position information of all the medical apparatuses 500 and the present position information of all the head mounted display 100 acquired at step S100, the medical apparatus 500, visual recognition of the display unit of which by a user of the head mounted display 100i is difficult (step S110).

FIG. 8 is an explanatory diagram for explaining a method of specifying the medical apparatus 500, visual recognition of the display unit of which by the user of the head mounted display 100i is difficult. FIG. 8 represents a general visual field in a normal human. It is known that, in the case of one eye, the visual field of the normal human is about 60 degrees on the head top side, about 70 degrees on the foot side, about 90 degrees on the ear side, and about 120 degrees on the nose side. Visual field of 60 degrees in the horizontal direction on both sides of the nose can be simultaneously viewed by the right and left eyes. In the following explanation, the visual field that can be simultaneously viewed by both the eyes is also referred to as "both eye visual field". Similarly, a visual field that can be viewed by only the left eye is also referred to as "left eye visual field" and a visual field that can be viewed by only the right eye is also referred to as "right eye visual field". Note that, in FIG. 8, the visual field is specified by only the angles. However, distances may be taken into account in addition to the angles.

In step S110 of the information-for-presentation generation processing (FIG. 6), the generating unit 360 performs processing of the following procedures a1 to a3 and specifies the medical apparatus 500, the visual recognition of the display unit of which by the user of the head mounted display 100i is difficult.

(a1) The specifying unit 361 determines the present position and the direction of the head mounted display 100i from the present position information and the direction information of the head mounted display 100i acquired at step S108.

(a2) The specifying unit 361 specifies, as "the medical apparatus 500, visual recognition of the display unit of which by the user is difficult", the medical apparatus 500 present in a position not included in ranges of all of the both eye visual field, the left eye visual field, and the right eye visual field shown in FIG. 8 on the basis of the present position and the direction determined in the procedure a1.

(a3) When the present position of another head mounted display apparatus 100 is present near a straight line section between the present position of the head mounted display 100i and the position of the medical apparatus 500, the specifying unit 361 specifies the medical apparatus 500 as "the medical apparatus 500, visual recognition of the display unit of which by the user is difficult". Note that the procedure a3 is executed on only the medical apparatus 500 not covered by the procedure a2.

A specific example of step S110 is explained with reference to FIG. 7. In the following explanation, the head mounted display 100i is the head mounted display 100a. The specifying unit 361 determines a present position UP1 and a direction UD1 on the basis of present position information and direction information of the head mounted display 100a (the procedure a1). The specifying unit 361 specifies, as the medical apparatus 500, visual recognition of the display unit of which by the user of the head mounted display 100a is difficult, the medical apparatuses 503 and 50n present in the positions MP3 and MPn not included in the both eye visual field, the left eye visual field, and the right eye visual field of the user of the head mounted display 100a on the basis of the present position UP1 and the direction UD1 (the procedure a2). Since the present position of another head mounted display 100 is absent near a straight line section between the present position UP1 of the head mounted display 100a and the position MP1 of the medical apparatus 501, the specifying unit 361 determines that the medical apparatus 501 is not the medical apparatus 500, the visual recognition of which is difficult. Similarly, since the present position of another head mounted display 100 is absent near straight line sections between the present position UP1 and the position MP2 of the medical apparatus 502, between the present position UP1 and the position MP4 of the medical apparatus 504, and between the present position UP1 and the position MP5 of the medical apparatus 505, the specifying unit 361 determines that the medical apparatuses 502, 504, and 505 are not the medical apparatus 500, the visual recognition of which is difficult (the procedure a3). As a result of the procedures, when the head mounted display 100*i* is the head mounted display 100*a*, the specifying unit 361 specifies the medical apparatuses 503 and 50*n* as the medical apparatus 500, the visual recognition of the display unit of which by the user of the head mounted display 100*a* is difficult.

In the following explanation, the head mounted display 100*i* is the head mounted display 100*n*. The specifying unit 361 determines a present position UPn and a direction UDn on the basis of present position information and direction information of the head mounted display 100*n* (the procedure a1). The specifying unit 361 specifies, as the medical apparatus 500, visual recognition of the display unit of which by the user of the head mounted display 100*n* is difficult, the medical apparatus 50*n* present in the position MPn not included in the both eye visual field, the left eye visual field, and the right eye visual field of the user of the head mounted display 100*n* on the basis of the present position UPn and the direction UDn (the procedure a2). Since present position UP2 of another head mounted display 100*b* is present near a straight line section between the present position UPn of the head mounted display 100*n* and the position MP1 of the medical apparatus 501, the specifying unit 361 determines that visual recognition of the display unit of the medical apparatus 501 is difficult. Similarly, since the present position UP1 of another head mounted display 100*a* is present near a straight line section between the present position UPn and the positions MP2 and MP4 of the medical apparatuses 502 and 504, the specifying unit 361 determines that visual recognition of the display units of the medical apparatuses 502 and 504 is difficult. Similarly, since the present position of another head mounted display 100 is absent near a straight line section between the present position UPn and the positions MP3 and MP5 of the medical apparatuses 503 and 505, the specifying unit 361 determines that visual recognition of the display units of the medical apparatuses 503 and 505 is not difficult (the procedure a3). As a result of the procedures, when the head mounted display 100*i* is the head mounted display 100*n*, the specifying unit 361 specifies the medical apparatuses 501, 502, 504, and 50*n* as the medical apparatus 500, the visual recognition of the display unit of which by the user of the head mounted display 100*n* is difficult.

As explained above, according to the procedure a2, the specifying unit 361 of the generating unit 360 can specify, taking into account the general visual field of the human, the medical apparatus 500, the visual recognition of the display unit of which by the user of the head mounted display 100*i* is difficult. Further, according to the procedure a3, the specifying unit 361 of the generating unit 360 can also specify the medical apparatus 500, visual recognition of the display unit of which by the user is difficult because of the presence of the user of another head mounted display 100, although the medical apparatus 500 is present within the range of the visual field.

As explained above, according to steps S100 to S110, the specifying unit 361 can specify the medical apparatus 500, visual recognition of the display unit of which is difficult, on the basis of the present position information and the direction information of the head mounted display 100 and the medical apparatus 500. Specifically, the specifying unit 361 can specify the medical apparatus 500, the display unit of which cannot or cannot easily be visually recognized by the user because the medical apparatus 500 is present at the dead angle of the user. The specifying unit 361 can also specify, taking into account the distances in addition to the angles, the medical apparatus 500, the display unit of which cannot or cannot easily be visually recognized by the user because the medical apparatus 500 is present in a place apart from the user. The specifying unit 361 can acquire information necessary in specifying the medical apparatus 500 via the first input-output unit 310 (the acquiring unit) and the second input-output unit 370 (the presenting unit). This is convenient because the user does not need to prepare data and the like in advance in using the information processing apparatus 300.

The specifying unit 361 of the generating unit 360 may specify the medical apparatus 500, the visual recognition of the display unit of which by the user of the head mounted display 100 is difficult, by executing procedures z1 to z6 explained below instead of the processing explained in steps S100 and S110 in FIG. 6. In this case, in the ROM 320 (or the external storage device 380) of the information processing apparatus 300, images of the display units of all the medical apparatuses 500 (the medical apparatuses 501 to 50*n*) connected to the information processing apparatus 300 are stored in advance.

(z1) The generating unit 360 sets "1" in the variable i used in the information-for-presentation generation processing.

(z2) The specifying unit 361 refers to the ith entry of the management table 382.

(z3) The specifying unit 361 acquires an "identifier" of the head mounted display 100 stored in the ith entry of the management table 382.

(z4) The specifying unit 361 instructs the head mounted display 100*i* to pick up an outside scene image using the camera 61 and acquires the picked-up outside scene image.

(z5) The specifying unit 361 performs image recognition of the outside scene image to thereby determine whether the images of the display units of the medical apparatuses 500 (the medical apparatuses 501 to 50*n*) stored in the ROM 320 are included in the outside scene image.

(z6) The specifying unit 361 specifies the medical apparatus 500, "the image of the display unit of which is determined as not being included in the outside scene image", as the medical apparatus 500, the visual recognition of the display unit of which by the user of the head mounted display 100*i* is difficult.

As explained above, according to the procedures z1 to z6, the specifying unit 361 can specify the medical apparatus 500, visual recognition of the display unit of which is difficult, on the basis of the image (the outside scene image) in the visual field direction of the user actually acquired by the camera 61 of the head mounted display 100*i*. Specifically, since the medical apparatus 500 is present at the dead angle of the user, the specifying unit 361 can specify the medical apparatus 500 that cannot or cannot easily be visually recognized by the user. The specifying unit 361 can specify, by adjusting the accuracy of the image recognition in the procedure z5, even the medical apparatus 500 that cannot or cannot easily be visually recognized by the user because the medical apparatus 500 is present in a place apart from the user. Further, the specifying unit 361 can specify the medical apparatus 500, visual recognition of the display unit of which is difficult, on the basis of the actual visual field of the user of the head mounted display 100*i*. More specifically, the specifying unit 361 can specify the medical apparatus 500 that cannot or cannot easily be visually recognized by the user because the display unit is not opposed to the visual line of the user (e.g., when the user looks down or when the display unit of the medical apparatus 500 is directed in the same direction as the visual line of the user), although the medical apparatus 500 is not present at the dead angle of the user and is present in a place near from the user. The specifying unit 361 can acquire information necessary in specifying the medical apparatus 500 via the second input-output unit 370 (a providing unit). This is convenient because the user does not need to prepare data and the like in advance in using the information processing apparatus 300.

In step S112 of the information-for-presentation generation processing (FIG. 6), the generating unit 360 generates information for presentation PNi to be transmitted to the head mounted display 100*i* using the medical apparatus information acquired from the medical apparatus 500, the visual recognition of the display unit of which by the user of the head mounted display 100*i* is difficult, specified in step S110 among the medical apparatus information of the medical apparatuses 501 to 50*n* acquired by the first input-output units 311 to 31*n*.

FIGS. 9A and 9B are explanatory diagrams for explaining a method of generating information for presentation. When there is only one medical apparatus 500, the visual recognition of the display unit of which by the user of the user of the head mounted display 100*i* is difficult, the generating unit 360 generates information for presentation PN by converting an image included in medical apparatus information CP1 of the medical apparatus 500 according to the specifications of the video signal specified in the common video specification 381 (FIG. 9A). In this conversion, in particular, when an aspect ratio of the image included in the medical apparatus information CP1 and an aspect ratio of the image specified in the common video specification 381 are different, the generating unit 360 enlarges or reduces the image included in the medical apparatus information CP1 while maintaining the aspect ratio of the image. Then, margin portions without an image (represented by hatching in the figure) are formed in the longitudinal direction or the lateral direction of the information for presentation PN.

The generating unit 360 executes any one of procedures b1 and b2 concerning the margin portions. Consequently, the margin portions are displayed as virtual images on the head mounted display 100. It is possible to suppress the margin portions from blocking the visual field of the user.

(b1) The generating unit 360 inserts black dummy dot data into the margin portions of the information for presentation PN.

(b2) The generating unit 360 sets, for the margin portions of the information for presentation PN, a signal (an Enable signal) for switching enabled/disabled of image light generation in the right display driving unit 22 and the left display driving unit 24 of the head mounted display 100 to a Lo value (a value indicating disabled).

Consequently, the aspect ratio of the image included in the information for presentation PN does not change. Concerning an image (e.g., a sill image and a moving image, a CT image, an MRI image, or an X-ray image) in a medical site where the information processing apparatus 300 is used, it is preferable to strictly maintain an aspect ratio of the image photographed in the medical apparatus 500 such that a sense of an actual size of the image visually recognized by the user is not spoiled. In that regard, if the aspect ratio of the image included in the medical apparatus information CP1 is maintained, it is possible to suppress unexpected distortion from occurring in medical apparatus information, for example, measured or picked up by the medical apparatus 500. Note that FIG. 9B shows information for presentation PNx in which distortion occurs as a result of not maintaining the aspect ratio of the image included in the medical apparatus for information CP1 and enlarging the image according to the aspect ratio of the image specified in the common video specification 381.

FIG. 10 is an explanatory diagram for explaining a method of generating information for presentation. When there are a plurality of medical apparatuses 500, visual recognition of the display units of which by the user of the head mounted display 100*i* is difficult, the generating unit 360 generates a first image in which images included in medical apparatus information (in an example shown in FIG. 10, medical apparatus information CP2 and CP3) of all the specified medical apparatuses 500, the visual recognition of which is difficult, are arranged. In this case, as in the case explained above, the generating unit 360 maintains an aspect ratio of the images included in the medical apparatus information. It is preferable that the images included in the medical apparatus information are arranged at an end of the first image. The generating unit 360 generates the information for presentation PN by converting the generated first image according to the specification of the video signal specified in the common video specification 381 (FIG. 10). Note that the generating unit 360 executes any one of the procedures b1 and b2 concerning a margin portion (represented by hatching) where the images included in the medical apparatus information are not arranged in the first image. Consequently, the margin portion is displayed as a virtual image on the head mounted display 100. It is possible to suppress the margin portion from blocking the visual field of the user.

In step S112 of the information-for-presentation generation processing (FIG. 6), the generating unit 360 causes the record of operation 384 to store the generated information for presentation PNi.

In step S114, the generating unit 360 transmits the generated information for presentation PNi to a second input-output unit 370*i* to which the head mounted display 100*i* is connected. The second input-output unit 370*i* converts an image included in the received information for presentation PNi according to a specification of a video signal of the head mounted display 100*i*. Note that, in this case, the second input-output unit 370*i* can refer to the "video specification" of the management table 382. After the conversion of the video specification, the second input-output unit 370*i* transmits the information for presentation PNi to the head mounted display 100*i*.

FIG. 11 is an explanatory diagram showing a state in which the information for presentation PNi is displayed as a virtual image on the head mounted display 100*i*. In the head mounted display 100*i* that receives the information for presentation PNi from the interface 180 or the radio communication unit 132, the display processing explained above by the image processing unit 160 is performed. As a result, image light guided to both the eye of the user of the head mounted display 100*i* is focused on the retinas of the user, whereby the user can visually recognize a virtual image VI of the information for presentation PNi in a visual field VR. The user can directly visually recognize, through the right optical-image display unit 26 and the left optical-image display unit 28, a state of a patient lying on an operating table (an outside scene SC). In an example shown in FIG. 11, in a virtual image VI (i) visually recognized by the user of the head mounted display 100*i*, the medical apparatus information CP2 acquired from the medical apparatus 503, visual recognition of which by the user of the head mounted display 100i is difficult, and the medical apparatus information CP3 acquired from the medical apparatus 50n are displayed.

FIG. 12 is an explanatory diagram showing a state in which the information for presentation is displayed as virtual images on a plurality of head mounted display 100 resent in different places. The second input-output unit 370 of the information processing apparatus 300 may perform fitting processing for matching the direction and the size of an image included in the information for presentation to the direction and the size of a target object included in the outside scene SC as shown in FIG. 12. In a medical site, the target object is, for example, a body of a patient or a part of the body. In order to realize the fitting processing, in step S114 of the information-for-presentation generation processing (FIG. 6), the second input-output unit 370 performs processing indicated by procedures c1 to c5 explained below after converting the image included in the information for presentation PNi according to the specification of the video signal of the head mounted display 100i.

(c1) The second input-output unit 370i instructs the head mounted display 100i to pick up an outside scene image using the camera 61 and acquires the picked-up outside scene image.

(c2) The second input-output unit 370i extracts features of a target object included in outside scene image using methods for image recognition explained in 1 and 2 below. Note that the methods 1 and 2 may be combined.

1. Detecting an edge (a feature) of the target object.
2. Detecting a marker (a feature) attached to the target object in advance. Note that, as the marker attached to the object, various kinds of markers can be used. For example, a tape, a sticker, a magic marker, a laser marker, and a magic tape (registered trademark) can be used. The number of markers attached to the target object is arbitrary.

(c3) The second input-output unit 370i extracts the feature of the target object by performing image recognition of the image included in the received information for presentation. In this case, the second input-output unit 370i can use methods for image recognition same as the methods for image recognition in 1 and 2 explained above.

(c4) The second input-output unit 370i corrects an image CP included in the information for presentation such that positions of the feature of the outside scene image extracted in the procedure c2 and the feature of the information for presentation extracted in the procedure c3 coincide with each other. Specifically, when the method 1 is used in the procedures c2 and c3, the second input-output unit 370i applies processing of at least one of enlargement, reduction, rotation, reversal, trimming, distortion, and removal of noise to the image CP included in the information for presentation such that positions of contours and characteristic parts coincide with each other in an edge of the outside scene image and an edge of the information for presentation. When the target object is an organism, the characteristic parts are a contour of an incised skin, a contour of an internal organ, joints, distal ends of arms and legs, blood vessels, bones, and the like. On the other hand, when the method 2 is used in the procedures c2 and c3, the second input-output unit 370i applies processing of at least one of enlargement, reduction, rotation, reversal, trimming, distortion, and removal of noise to the image CP included in the information for presentation such that positions of a marker of the outside scene image and a marker of the information for presentation coincide with each other.

Consequently, the second input-output unit 370 performs image recognition of an image in the visual field direction of the user of the head mounted display 100 (the head mounted display apparatus) to extract a feature of an object included in an outside scene and corrects, on the basis of the extracted feature, the information for presentation generated by the generating unit 360. Therefore, when invisible information such as a CT image, an MRI image, or an X-ray image is included in the information for presentation, it is possible to match the invisible information to the object (e.g., a body of a patient) included in the outside scene. As a result, it is possible to improve convenience for the user of the head mounted display 100i. The fitting processing is executed in the second input-output unit 370i connected to the specific head mounted display 100i. Therefore, a processing load is not applied to the second input-output units 370 connected to the other head mounted display 100. Further, the head mounted display 100i can receive the information for presentation after the fitting processing is applied. Therefore, the image processing unit 160 of the head mounted display 100i only has to directly display the received information for presentation. As a result, it is possible to simplify the configuration of the head mounted display 100.

In step S116 of the information-for-presentation processing (FIG. 6), the generating unit 360 increments the variable i. Thereafter, the generating unit 360 determines whether the variable i is not equal to or larger than n (step S118). When the variable i is smaller than n (step S118: NO), this means that the head mounted display 100 for which the initial processing does not end is present among the head mounted displays 100 connected to the second input-output unit 370. Therefore, the generating unit 360 shifts the processing to step S100 and continues the initial processing. On the other hand, when the variable i is equal to or larger than n (step S118: YES), this means that the initial processing ends concerning all the head mounted displays 100. Therefore, the generating unit 360 shifts the processing to the individual processing in step S120.

A-4-2. Individual Processing

In the individual processing, the generating unit 360 generates, on the basis of a request from the head mounted display 100, information for presentation including medical apparatus information acquired from the requested medical apparatus 500 and information acquired from an information source other than the requested medical apparatus 500.

In step S120 of the information-for-presentation generation processing (FIG. 6), the generating unit 360 determines whether an information source selection request is received from the head mounted display 100. The information source selection request means, for example, requests enumerated in d1 to d6 below.

(d1) A browsing request for medical apparatus information acquired by the medical apparatus 500
(d2) A telephone call request to the doctor PR in the external facility
(d3) A browsing request for data recorded in the in-hospital database OD
(d4) A browsing request for data recorded in the invisible information 383
(d5) A browsing request for data recorded in the record of operation 384
(d6) A browsing request for medical apparatus information of the medical apparatus 500, visual recognition of the display unit of which by the user of the head mounted display 100 is difficult An information source in the case of the request d1 is the medical apparatus 500. Similarly, an information source in the case of the request d2 is the doctor PR. An information source in the case of the request d3 is the database OD. An information source in the case of the request d4 is the invisible information 383. An information source in the case of the request d5 is the record of operation 384. An information source in the case of the request d6 is the medical apparatus 500, the visual recognition of which is difficult. The requests d1 to d6 may be issued independently or may be combined. The information source selection request is issued as appropriate according to operation by the user of the head mounted display 100.

The head mounted display 100 can transmit the information source selection request to the information processing apparatus 300, for example, according to procedures e1 to e5 explained below.

(e1) The user of the head mounted display 100 inputs a desired information source and information for specifying information in the information source via the input device (the touch pad, the cross key, the foot switch, the gesture, the microphone, etc.) of the head mounted display 100. If a sound input via the microphone is adopted as an input method, it is possible to greatly improve convenience for the user when the head mounted display 100 is used in a medical site where it is difficult for the user to operate the head mounted display 100 by hand. Note that, in the case of the requests d1 and d6, the input of the "information for specifying information in the information source" is unnecessary.

(e2) The input-information acquiring unit 110 of the head mounted display 100 acquires a signal corresponding to an operation input of the user and transmits the signal to the OS 150.

(e3) The OS 150 of the head mounted display 100 generates an information source selection request. Specifically, in the case of the request d1, the OS 150 generates an information source selection request including an identifier of the head mounted display 100 and an identifier for specifying the information source designated in the procedure e1. In the case of the requests d2 to d5, the OS 150 generates an information source selection request including the identifier of the head mounted display 100, the identifier for specifying the information source designated in the procedure e1, and information for specifying information in the information source. In the case of the request d6, the OS 150 generates an information source selection request including the identifier of the head mounted display 100, and present position information and direction information of the head mounted display 100. Note that the present position information and the direction information are information used for specifying "the medical apparatus 500, visual recognition of the display unit of which by the user is difficult" of the request d6 with the generating unit 360 and is equivalent to the information for specifying an information source.

(e4) The OS 150 of the head mounted display 100 transmits the information source selection request generated in the procedure e3 to the information processing apparatus 300 connected via the interface 180 and the radio communication unit 132.

(e5) The second input-output unit 370 of the information processing apparatus 300 transmits the received information source selection request to the generating unit 360.

When the information source selection request is received in the information-for-presentation generation processing (FIG. 6) (step S120: YES), in step S122, the generating unit 360 acquires the identifier of the head mounted display 100i, the information for specifying an information source, and the information in the information source included in the information source selection request. Further, when the present position information and the direction information are inserted as the information for specifying an information source, the generating unit 360 executes processing same as step S110 in FIG. 6 and specifies "the medical apparatus 500, visual recognition of the display unit of which by the user is difficult" obtained as an execution result. The head mounted display 100i indicates the head mounted display 100 that is an issue source of the information source selection request (i.e., the head mounted display 100 that is currently performing processing).

In step S124, the generating unit 360 accesses the designated information source and acquires the designated information. The generating unit 360 generates the information for presentation PNi for the head mounted display 100i using the acquired information and causes the record of operation 384 to store the generated information for presentation PNi. Note that a method of generation of the information for presentation by the generating unit 360 is as explained with reference to FIGS. 9 and 10.

FIGS. 13A and 13B are explanatory diagrams showing a first example of the information for presentation. FIG. 13A is an example of the information for presentation PN generated by the generating unit 360 when an X-ray image (CP4) of a patient stored in the invisible information 383 is designated in the information source selection request. Note that information for presentation same as the information for presentation shown in FIG. 13A is generated when the medical apparatus 500 (an X-ray image photographing apparatus) capable of acquiring invisible information is designated in the information source selection request.

FIG. 13B is an example of the information for presentation PN generated by the generating unit 360 when a timer for surgery functioning as the medical apparatus 500, a pulse rate meter functioning as the medical apparatus 500, and a biological monitor functioning as the medical apparatus 500 are designated. At ends of the information for presentation PN, present time CP5 acquired from the timer for surgery, an elapsed time CP7 from the start of surgery, an image CP6 of a pulse rate acquired from the pulse rate meter, and an image CP8 of a heart rate (HR), a blood pressure (SYS/DIA), and arterial oxygen saturation (SpO2) acquired from the biological monitor are arranged. Note that, when a plurality of information sources are designated as shown in FIG. 13B, the head mounted display 100 may designate "arrangement" and "magnitude" of information in the information sources in the information source selection request.

FIGS. 14A and 14B are explanatory diagrams showing a second example of the information for presentation. FIG. 14A is an example of the information for presentation PN generated by the generating unit 360 when an academic book (CP9) stored in the in-hospital database OD and operation procedure information (CP10) stored in the in-hospital database OD are designated in the information source selection request. FIG. 14B is an example of the information for presentation PN generated by the generating unit 360 when a visible light camera functioning as the medical apparatus 500 for photographing a still image and a moving image of a site of operation and a telephone call to the doctor PR in the external facility are designated in the information source selection request.

FIG. 15 is an explanatory diagram showing a third example of the information for presentation. FIG. 15 is an example of the information for presentation PN generated by the generating unit 360 when a biological monitor functioning as the medical apparatus 500 is designated in the information source selection request. The biological monitor shown in FIG. 15 does not include an interface that can be connected to the first input-output unit 310. However, if the information processing apparatus 300 includes the visible light camera and the visible light camera photographs a screen (CP13) of the biological monitor, the generating unit 360 can generate the information for presentation PN as shown in FIG. 15 using medical apparatus information received from a medical apparatus not including an interface that can be connected to the first input-output unit 310.

In step S126 of the information-for-presentation generation processing (FIG. 6), the generating unit 360 transmits the information for presentation PNi generated in step S124 to the second input-output unit 370i to which the head mounted display 100i is connected. Thereafter, the generating unit 360 shifts the processing to step S120 and continues monitoring of reception of the information source selection request. The second input-output unit 370i, which receives the information for presentation PNi, converts an image included in the received information for presentation PNi according to the specification of the video signal of the head mounted display 100i. In this case, the second input-output unit 370i may execute the fitting processing. Details are as explained in step S114.

In the head mounted display 100i that receives the information for presentation PNi via the interface 180 or the radio communication unit 132, the display processing by the image processing unit 160 is performed. As a result, the user of the head mounted display 100i, which transmits the information source selection request, can visually recognize a virtual image of the information for presentation PNi including the information acquired from the information source designated in the information source selection request.

As explained above, with the information processing apparatus 300 in the first embodiment, the generating unit 360 generates the information for presentation PN including at least a part of a plurality of kinds of medical apparatus information acquired by the first input-output unit 310 (the acquiring unit, the first input-output units 311 to 31n). Therefore, it is possible to unify information (medical apparatus information) of the variety of medical apparatuses 500 (the medical apparatuses 501 to 50n) connected to the first input-output unit 310 of the information processing apparatus 300. In the initial processing of the information-for-presentation generation processing, the generating unit 360 generates the information for presentation PN including at least the medical apparatus information acquired by the medical apparatus 500, visual recognition of the display unit of which by the user of the head mounted display 100 (the image display apparatus) is difficult. Therefore, it is possible to extract information from the unified medical apparatus information under a condition that information is the medical apparatus information of the medical apparatus 500, the visual recognition of the display unit of which is difficult, and include the extracted information in the information for presentation PN. As a result, it is possible to realize the information processing apparatus 300 capable of unifying the information concerning the variety of medical apparatuses 500 (the medical apparatuses 501 to 50n) and capable of easily filtering information from the unified information and generating information to be displayed on the head mounted display 100.

Further, the information processing apparatus 300 in the first embodiment includes the invisible information 383 (the invisible-information storing unit). Therefore, it is possible to unify the invisible information stored in the invisible information 383 in addition to the medical apparatus information of the variety of medical apparatuses 500 (the medical apparatuses 501 to 50n) connected to the first input-output unit 310 (the first input-output units 311 to 31n) of the information processing apparatus 300. The generating unit 360 can extract, from the unified information, for example, as shown in FIGS. 13A and 13B, invisible information, which is information not appearing in the external appearance of the object, such as a CT image, an MRI image, a X-ray image, a transparent image, an ultrasonic diagnosis image, an endoscope image, or a thermography image and generate the information for presentation PN to be displayed on the head mounted display 100 (the image display apparatus). As a result, the user of the head mounted display 100 connected to the information processing apparatus 300 can visually recognize the invisible information. This leads to improvement of convenience of the head mounted display 100. Similarly, the generating unit 360 can extract medical apparatus information acquired by the medical apparatus 500 for acquiring the invisible information, which is information not appearing in the external appearance of the object, such as a CT image, an MRI image, a X-ray image, a transparent image, an ultrasonic diagnosis image, an endoscope image, or a thermography image and generate the information for presentation PN to be displayed on the head mounted display 100. As a result, the user of the head mounted display 100 connected to the information processing apparatus 300 can visually recognize the invisible information. This leads to improvement of convenience of the head mounted display 100.

Further, with the information processing apparatus 300 in the first embodiment, the generating unit 360 can extract medical apparatus information acquired by the medical apparatus 500 for acquiring a still image and a moving image of a site of operation, that is, an image of treatment of a patient and generate the information for presentation PN to be displayed on the head mounted display 100 (the image display apparatus). As a result, the user of the head mounted display 100 connected to the information processing apparatus 300 can visually recognize the image of the treatment of the patient. This leads to improvement of convenience of the head mounted display 100.

As explained above, with the information process ing system 1000 in the first embodiment, it is possible to realize the information processing system 1000 capable of unifying, in the information processing apparatus 300, the information (the medical apparatus information) of the variety of medical apparatuses 500 (the medical apparatuses 501 to 50n) and capable of easily filtering information from the unified information to generate the information for presentation PN and causing the user of the head mounted display 100 (the head mounted display apparatus) of the so-called transmission type to visually recognize the generated information for presentation PN as a virtual image.

A-5. Additional Processing

Not that, in the information-for-presentation generation processing (FIG. 6), additional processing explained below may be further executed. The additional processing may be added independently or may be added in combination.

A-5-1. Additional Processing 1

In additional processing 1, the information processing apparatus 300 performs color conversion processing for information for presentation. Specifically, the second input-output unit 370, which receives the information for presentation from the generating unit 360, causes the camera 61 of the head mounted display 100 to acquire an outside scene image. The second input-output unit 370 carries out color conversion processing for improving visibility of an image included in the information for presentation according to the brightness, the contrast, the chroma, and the hue of the acquired outside scene image. For example, the second input-output unit 370 can perform color conversion processing for converting the hue of the image included in the information for presentation into a complementary color of the hue of the outside scene image.

In this way, with the additional processing 1, it is possible to further improve visibility of the virtual image VI for the user of the head mounted display 100.

A-5-2. Additional Processing 2

In additional processing 2, the information processing apparatus 300 realizes a so-called stabilizer function for suppressing a shake of the virtual image VI incidental to a small shift of the head of the user of the head mounted display 100. Specifically, the second input-output unit 370, which receives the information for presentation from the generating unit 360, repeats, at every predetermined time, the fitting processing explained in the procedures c1 to c4 and the transmission of the information for presentation in steps S114 and S126 of the information-for-presentation generation processing. Consequently, the photographing of an outside scene image and the correction and the display of the image included in the information for presentation are repeated at every predetermined time. Therefore, it is possible to display, as the virtual image VI, the information for presentation following the movement over time of the head of the user.

However, when the information for presentation often changes following a slight movement or sway of the head of the user of the head mounted display 100, it is likely that eyestrain of the user is caused and concentration of the user is prevented. Therefore, the second input-output unit 370 may further perform processing indicated by procedures f1 and f2 explained below between the procedure c1 and the procedure c2.

(f1) The second input-output unit 370 calculates a change amount of an RGB histogram between the outside scene image photographed in the procedure c1 and the outside scene image photographed in the procedure c1 of the fitting processing executed last time.

(f2) The second input-output unit 370 continues the processing of the procedure c2 and the subsequent procedures when the change amount calculated in the procedure f1 exceeds a predetermined threshold.

In this way, with the additional processing 2, when the change amount between the outside scene image in the fitting processing executed last time and the outside scene image in the fitting processing currently being executed is small, that is, when the movement of the head of the user of the head mounted display 100 is very small, the second input-output unit 370 does not perform the correction of the image included in the information for presentation. As a result, it is possible to suppress the information for presentation from frequently changing following the very small movement or sway of the head of the user of the head mounted display 100. Therefore, it is possible to suppress the eyestrain and the deterioration in the concentration of the user. Note that ON/OFF of the stabilizer function may be able to be designated by the user.

A-5-3. Additional Processing 3

In additional processing 3, the information processing apparatus 300 changes, according to the distance between the image display unit 20 of the head mounted display 100 and an object present in the visual field direction of the user, the size of the display of the image included in the information for presentation displayed as the virtual image VI.

Specifically, the second input-output unit 370, which receives the information for presentation from the generating unit 360, can perform processing indicated by procedures g1 to g3 explained below instead of the fitting processing explained in the procedures c1 to c4. Note that, when this processing is carried out, the head mounted display 100 further includes a range finding sensor. The range finding sensor is a sensor for acquiring the distance between the object present in the visual field direction of the user and the image display unit 20 using reflected light. For example, the range finding sensor can be arranged near the camera 61.

(g1) The second input-output unit 370 periodically acquires a measurement value of the range finding sensor from the head mounted display 100.

(g2) The second input-output unit 370 determines an enlargement ratio (or a reduction ratio) according to the acquired measurement value of the range finding sensor.

(g3) The second input-output unit 370 applies at least one of enlargement, reduction, rotation, reversal, trimming, distortion, and removal of noise to the image included in the information for presentation using the determined enlargement or reduction ratio.

In this way, with the additional processing 3, the second input-output unit 370 can change, according to the distance between the object present in the visual field direction of the user of the head mounted display 100 and the image display unit 20, the size of the display of the information for presentation displayed as the virtual image VI. Therefore, it is possible to improve convenience for the user in the head mounted display 100.

B. Second Embodiment

In a second embodiment of the invention, a configuration for automatically determining a medical apparatus, visual recognition of a display unit of which by a user of a head mounted display apparatus is difficult, on the basis of a table is explained. In the following explanation, only components having configurations and operations different from the configurations and the operations in the first embodiment are explained. Note that, in the figures, components same as the components in the first embodiment are denoted by the same reference numerals and signs. Detailed explanation of the components is omitted.

B-1. Configuration of an Information Processing System

The schematic configuration of an information processing system 1000a in the second embodiment is substantially the same as the schematic configuration in the first embodiment shown in FIG. 1. However, the information processing system 1000a in the second embodiment includes an information processing apparatus 300a instead of the information processing apparatus 300.

B-2. Configuration of the Information Processing Apparatus

FIG. 16 is a block diagram functionally showing the configuration of the information processing apparatus 300a in the second embodiment. The information processing apparatus 300a in the second embodiment is different from the information processing apparatus 300 in the first embodiment in that the information processing apparatus 300a includes a generating unit 360a instead of the generating unit 360, includes a specifying unit 361a instead of the specifying unit 361, and includes an external storage device 380a instead of the external storage device 380. The generating unit 360a and the specifying unit 361a are different from the generating unit 360 and the specifying unit 361 in the first embodiment in processing contents in the information-for-presentation generation processing. Details are explained below. The external storage device 380a further includes a position table 385 functioning as an arrangement storing unit in addition to the components explained in the first embodiment.

FIG. 17 is an explanatory diagram showing an example of the position table 385. The position table 385 is a table for specifying the medical apparatuses 500, visual recognition of the display units of which by the users of the head mounted displays 100a to 100n is difficult. The position table 385 is used in the information-for-presentation generation processing.

In the position table 385 in this embodiment, an identifier, an apparatus 1, an apparatus 2, an apparatus 3, an apparatus 4, and an apparatus 5 are stored in association with one another. In the "identifier", unique identifiers for identifying the head mounted displays 100 connected to the second input-output unit 370 from one another are stored. In the "apparatus 1" to the "apparatus 5", concerning the head mounted displays 100 identified by the identifiers, identifiers of the medical apparatuses 500, visual recognition of the display units of which by the user is difficult, are stored.

In an example shown in FIG. 17, it is seen that the medical apparatuses 500, the visual recognition of the display units of which by the user of the head mounted display 100 is difficult, identified by the identifier "1" are the medical apparatus 503 and the medical apparatus 50n (an entry E01). Similarly, it is seen that the medical apparatuses 500, the visual recognition of the display units of which by the user of the head mounted display 100 is difficult, identified by the identifier "2" are the medical apparatus 503, the medical apparatus 505, and the medical apparatus 50n (an entry E021).

B-3. Configuration of the Head Mounted Display Apparatus

The schematic configuration of the head mounted display 100 in the second embodiment is the same as the schematic configuration in the first embodiment shown in FIG. 5.

B-4. Information-for-Presentation Generation Processing

FIG. 18 is a flowchart showing a procedure of the information-for-presentation generation processing in the second embodiment. The flowchart in the second embodiment is different from the flowchart in the first embodiment shown in FIG. 6 in that the flowchart in the second embodiment does not include step S100 and includes steps S200 to S204 instead of steps S104 to S112. The other steps are the same as the steps in the first embodiment.

In step S200 of the information-for-presentation generation processing (FIG. 18), the specifying unit 361a of the generating unit 360a refers to an ith entry of the position table 385. The specifying unit 361a of the generating unit 360a acquires the "identifier" of the head mounted display 100 stored in the ith entry of the position table 385 and the "apparatuses 1 to 5" (step S202).

In step S204, the generating unit 360a generates the information for presentation PNi to be transmitted to the head mounted display 100i using medical apparatus information acquired from the medical apparatus 500 having the identifier acquired in step S202, that is, the medical apparatus 500, visual recognition of the display unit of which by the user of the head mounted display 100i is difficult, among the medical apparatus information of the medical apparatuses 501 to 50n acquired by the first input-output units 311 to 31n. A method of generating the information for presentation is the same as the method in the first embodiment. Therefore, explanation of the method is omitted.

As explained above, with the information processing apparatus 300a in the second embodiment, the specifying unit 361a of the generating unit 360a can automatically specify the medical apparatus 500, the visual recognition of the display unit of which by the user of the head mounted display 100 is difficult, using the position table 385 (the arrangement storing unit) that stores the information for specifying the medical apparatus 500, the visual recognition of the display unit of which by the user of the head mounted display 100 (the image display apparatus) is difficult. Specifically, the specifying unit 361a can specify the medical apparatus 500, the display unit of which cannot or cannot easily be visually recognized by the user because the medical apparatus 500 is present at a dead angle of the user. The specifying unit 361a can also specify the medical apparatus 500, the display unit of which cannot or cannot easily be visually recognized by the user because the medical apparatus 500 is present in a place apart from the user. Further, the specifying unit 361a can specify the medical apparatus 500 that cannot or cannot easily be visually recognized by the user because the display unit is not opposed to the visual line of the user, although the medical apparatus 500 is not present at the dead angle of the user and is present in a place near from the user. The specifying unit 361a can acquire information necessary in specifying the medical apparatus 500 from the position table 385 prepared in advance. Therefore, even when the medical apparatus 500 connected to the first input-output unit 310 of the information processing apparatus 300a and the head mounted display 100 connected to the second input-output unit 370 of the information processing apparatus 300a do not include detecting means for position information, the specifying unit 361a can specify the medical apparatus 500, the visual recognition of the display unit of which by the user of the head mounted display 100 is difficult.

B-5. Additional Processing

Note that, in the information-for-presentation generation processing (FIG. 18) in the second embodiment, additional processing same as the additional processing in the first embodiment explained in "A-5-1. Additional processing 1" to "A-5-3. Additional processing 3" may be executed.

C. Modifications

In the embodiments, a part of the components realized by hardware may be replaced with software. Conversely, a part of the components realized by software may be replaced with hardware. Besides, modifications explained below are also possible.

Modification 1

In the embodiments, the configuration of the information processing system is illustrated. However, the configuration of the information processing system can be arbitrarily determined without departing from the spirit of the invention. For example, addition, deletion, conversion, and the like of the apparatuses configuring the information processing system can be performed. Further, a change of the network configuration of the apparatuses configuring the information processing system can be performed.

For example, the management table of the information processing apparatus, the invisible information, the record of operation, and the position table may be stored in the database OD connected to the in-hospital LAN. The database OD is not limitedly provided in the hospital and may be provided on the outside (e.g., a cloud server provided outside the hospital) via the Internet INT.

Modification 2

In the embodiments, the configuration of the information processing apparatus is illustrated. However, the configuration of the information processing apparatus can be arbitrarily determined without departing from the spirit of the invention. For example, addition, deletion, conversion, and the like of the components can be performed.

For example, the information processing apparatus may include various input devices such as a touch panel, an input button, a keyboard, a mouse, a microphone, and a camera. Similarly, the information processing apparatus may include various output devices such as a display, an indicator, and a printer for outputting a simple log concerning an operation.

For example, in the embodiments, the functions in the generating unit and the second input-output unit (the providing unit) are described as being realized by the CPU expanding the computer program stored in the ROM or the hard disk on the RAM and executing the computer program. However, these functions may be realized using an ASIC (Application Specific Integrated Circuit) designed to realize the functions.

For example, the information processing apparatus includes a display, a present-position acquiring unit that acquires position information, and a direction sensor. Then, the CPU of the information processing apparatus may be configured to perform processing same as the initial processing in the information-for-presentation generation processing (FIG. 6) in the first embodiment using the position information and the direction information of the information processing apparatus, specify the medical apparatus, visual recognition of the display unit of which by the user of the information processing apparatus is difficult, and cause the display of the information processing apparatus to display medical apparatus information acquired from the specified medical apparatus. Consequently, the user standing near the information processing apparatus can check the display provided in the information processing apparatus. Consequently, it is possible to allow even a staff member not having the head mounted display (the image display apparatus) according to the invention to easily grasp information.

For example, the information processing apparatus includes a camera that acquires an outside scene image in a direction in which the information processing apparatus faces. Then, the CPU of the information processing apparatus may be configured to perform processing same as the initial processing using the procedures z1 to z6 of the information-for-presentation generation processing (FIG. 6) in the first embodiment, specify the medical apparatus, visual recognition of the display unit of which by the user of the information processing apparatus is difficult, and cause the display of the information processing apparatus to display medical apparatus information acquired from the specified medical apparatus. Consequently, the user standing near the information processing apparatus can check the display provided in the information processing apparatus. Consequently, it is possible to allow even a staff member not having the head mounted display (the image display apparatus) according to the invention to easily grasp information.

For example, the information processing apparatus includes a display. Identifiers of the medical apparatuses, visual recognition of the display units of which by the user of the information processing apparatus is difficult, are stored in the position table. Then, the CPU of the information processing apparatus may be configured to perform processing same as the initial processing in the information-for-presentation generation processing (FIG. 18) in the second embodiment, specify the medical apparatus, visual recognition of the display unit of which by the user of the information processing apparatus is difficult, and cause the display of the information processing apparatus to display medical apparatus information acquired from the specified medical apparatus. Consequently, the user standing near the information processing apparatus can check the display provided in the information processing apparatus. Consequently, it is possible to allow even a staff member not having the head mounted display (the image display apparatus) according to the invention to easily grasp information.

For example, the function of the providing unit in the initial processing using the procedures z1 to z6 of the information-for-presentation generation processing (FIG. 6) in the first embodiment may be realized in the head mounted display. In this case, after the medical apparatus, visual recognition of the display unit of which by the user is difficult, is specified in the head mounted display, the interface (a notifying unit) of the head mounted display notifies the information processing apparatus of an identifier of the specified medical apparatus. The information processing apparatus only has to generate information for presentation according to procedures same as the procedures in the first embodiment using medical apparatus information acquired from the medical apparatus having the notified identifier. Consequently, the specifying unit can be provided in the head mounted display. Therefore, it is possible to reduce a processing load in the information processing apparatus.

Modification 3

In the embodiments, the configuration of the head mounted display is illustrated. However, the configuration of the head mounted display can be arbitrarily determined without departing from the spirit of the invention. For example, addition, deletion, conversion, and the like of the components can be performed. For example, the control unit and the image display unit can be connected via a wireless signal transmission line such as a wireless LAN, infrared communication, or Bluetooth. For example, as the power supply, a primary battery, a fuel battery, a solar battery, a thermal battery, or the like may be adopted.

The allocation of the components to the control unit and the image display unit in the embodiment is only an example. Various forms can be adopted. For example, forms explained below may be adopted. (i) A form in which processing function such as a CPU and a memory are mounted on the control unit and only a display function is mounted on the image display unit. (ii) A form in which the processing functions such as the CPU and the memory are mounted on both of the control unit and the image display unit. (iii) A form in which the control unit and the image display unit are integrated (e.g., a form in which the control unit is included in the image display unit and functions as an eyeglass type wearable computer). (iv) A form in which a smart phone or a portable game machine is used instead of the control unit. (v) A form in which the control unit and the image display unit are configured to be capable of communicating by radio and wirelessly supplying electric power, whereby a cable is removed.

For example, the input-information acquiring unit may acquire an operation input from the user using various methods other than the method illustrated in the embodiments. For example, the input-information acquiring unit may acquire an operation input by a foot switch (a switch operated by the foot of the user). For example, a visual-line detecting unit such as an infrared sensor may be provided in the image display unit to detect the visual line of the user and acquire an operation input by a command associated with the movement of the visual line. For example, a camera may be used to detect a gesture of the user and acquire an operation input by a command associated with the gesture. In the gesture detection, a fingertip of the user, a ring put on a finger of the user, a medical instrument held by the user, or the like can be set as a mark for movement detection. If an operation input by the foot switch or the visual line can be acquired, the input-information acquiring unit can easily acquire an operation input from the user even in a medical site where it is difficult for the user to release the hand from the head mounted display apparatus.

For example, in the embodiments, the head mounted display is the transmissive head mounted display of the binocular type. However, the head mounted display may be a head mounted display of a monocular type. The head mounted display may be configured as a non-transmissive head mounted display with which transmission of an outside scene is blocked in a state in which the user wears the head mounted display. In the embodiments, the head mounted display is the head mounted display, the image display unit of which is worn like eyeglasses. However, the head mounted display may be a head mounted display that adopts an image display unit having another shape such as an image display unit of a type worn like a hat. As the earphones, an ear hook type or a head band type may be adopted. The earphones may be omitted. Further, for example, the head mounted display may be configured as a head-up display (HUD) mounted on vehicles such as an automobile and an airplane. Besides, the head mounted display may be configured as a head mounted display incorporated in a body protector such as a helmet.

FIGS. 19A and 19B are explanatory diagrams showing the configuration of an external appearance of a head mounted display in a modification. In the case of an example shown in FIG. 19A, an image display unit 20a includes a right optical-image display unit 26a instead of the right optical-image display unit 26 and includes a left optical-image display unit 28a instead of the left optical-image display unit 28. The right optical-image display unit 26a is formed smaller than the optical member in the first embodiment and arranged obliquely above the right eye of a user when the user wears the head mounted display. Similarly, the left optical-image display unit 28a is formed smaller than the optical member in the first embodiment and arranged obliquely above the left eye of the user when the user wears the head mounted display. In the case of an example shown in FIG. 19B, an image display unit 20b includes a right optical-image display unit 26b instead of the right optical-image display unit 26 and includes a left optical-image display unit 28b instead of the left optical-image display unit 28. The right optical-image display unit 26b is formed smaller than the optical member in the first embodiment and arranged obliquely below the right eye of a user when the user wears the head mounted display. The left optical-image display unit 28b is formed smaller than the optical member in the first embodiment and arranged obliquely below the left eye of the user when the user wears the head mounted display. In this way, the optical-image display units only have to be arranged near the eyes of the user. The size of the optical members forming the optical image display unit is arbitrary. The head mounted display can also be realized as a head mounted display in which the optical-image display units cover only a part of the eyes of the user, in other words, the optical-image display units do not completely cover the eyes of the user.

For example, in the embodiments, the display driving unit includes the backlight, the backlight control unit, the LCD, the LCD control unit, and the projection optical system. However, this form is only an example. In addition to or instead of these components, the display driving unit may include components for realizing other systems. For example, the display driving unit may emit image light using a front light system or a reflection system. For example, the display driving unit may include an organic EL (Organic Electro-Luminescence) display, an organic EL control unit, and a projection optical system. For example, the display driving unit can also include a digital micro mirror device or the like instead of the LCD. For example, it is also possible to apply the invention to a head mounted display apparatus of a laser retina projection type.

Modification 4

In the embodiment, an example of the information-for-presentation generation processing is explained. However, the procedure of the information-for-presentation generation processing is only an example. Various modifications of the procedure are possible. For example, a part of the steps may be omitted or other steps may be added. The order of the steps to be executed may be changed.

In the initial processing in the information-for-presentation generation processing in the first embodiment (FIG. 6), the medical apparatus, visual recognition of the display unit of which by the user of the head mounted display is difficult, is specified using the present position information and the direction information of the head mounted display and the position information of the medical apparatuses. However, the medical apparatus, visual recognition of the display unit of which by the user of the head mounted display is difficult, may be specified by combining the movements (the speed, the acceleration, the angular velocity, the direction, and a change in the direction) of the head of the user obtained by the 9-axis sensor of the head mounted display.

For example, the initial processing is serially performed using the variable i concerning the plurality of head mounted displays connected to the second input-output unit. However, the initial processing explained with reference to FIGS. 6 and 18 may be executed in parallel concerning the plurality of head mount displays connected to the second input-output unit.

For example, as the invisible information explained in the embodiments, a two-dimensionally represented image is assumed. However, an apparatus capable of photographing a three-dimensional invisible image may be connected as the medical apparatus. The invisible information stored in the external storage device may be a three-dimensional model created from a plurality of images picked up using an image pickup device. When the three-dimensionally represented invisible information is used, the generating unit performs rendering of the three-dimensional model prior to generation of the information for presentation. The generating unit generates the information for presentation using an image after the rendering. Consequently, it is possible to visually recognize information not appearing in an external appearance of a target object from various directions.

For example, the head mounted display, which receives the information for presentation, may increase or reduce the size of display of the image included in the information for presentation displayed as the virtual image VI. Similarly, the head mounted display may hide the image included in the information for presentation according to a request of the user. The head mounted display may apply color conversion to the image included in the information for presentation. If a sound input via a microphone is adopted as a method of inputting a request from the user, it is possible to greatly improve convenience for the user when the head mounted display is used in a medical site where it is difficult for the user to operate the head mounted display using the hand.

For example, any one of the initial processing and the individual processing in the information-for-presentation generation processing may be omitted. The initial processing does not have to be executed immediately after the information-for-presentation generation processing is started. Processing similar to the initial processing may be executed as appropriate according to a request from the user or other applications.

Modification 5

In the embodiments, the examples of the common video specification, the management table, and the position table are explained. However, the details of the common video specification, the management table, and the position table are only an example. Various changes are possible. For example, addition, deletion, and change of fields (items) can be performed. The management table and the position table may be divided into a plurality of tables and normalized.

For example, in the management table, voice prints of the users of the head mounted displays may be stored instead of the identifiers for identifying the head mounted displays from one another or together with the identifiers. Consequently, the information processing apparatus can acquire, on the basis of the voice print of the user acquired via the microphone, the role and the video specification of the head mounted display used by the user and execute the information-for-presentation generation processing.

For example, in the management table, information used for communication between the head mounted displays and the information processing apparatus (e.g., IP addresses, MAC addresses, and encryption keys of the head mounted displays) may be stored in association with the identifiers of the head mounted displays. In the management table, actual video specifications themselves (i.e., items same as the items stored in the common video specification) adopted in the head mounted displays may be stored instead of the "video specification" representing patterns of specifications of video signals.

For example, in the position table, the identifiers of the maximum five apparatuses, visual recognition of the display units of which by the users of the head mounted displays is difficult, can be stored in association with the identifiers of the head mounted displays. However, in the position table, any number of "apparatus" fields can be included in the position table.

Modification 6

The invention is not limited to the embodiments, the examples, and the modifications explained above and can be realized in various configurations without departing from the spirit of the invention. For example, the technical features in the embodiments, the examples, and the modifications corresponding to the technical features in the aspects described in the summary of invention can be replaced or combined as appropriate in order to solve a part or all of the problems explained above or attain apart or all of the effects explained above. Unless the technical features are explained as essential features in this specification, the technical features can be deleted as appropriate.

REFERENCE SIGNS LIST

10 Control unit
20 Image display unit
22 Right display driving unit
24 Left display driving unit
26 Right optical-image display unit
28 Left optical-image display unit
32 Right earphone
34 Left earphone
40 Cable
51 Transmitting unit
52 Transmitting unit
53 Receiving unit
54 Receiving unit
61 Camera (image acquiring unit)
110 Input-information acquiring unit
100 Head mounted display (image display apparatus, head mounted display apparatus)
120 Storing unit
130 Power supply
140 CPU
160 Image processing unit
170 Sound processing unit
180 Interface (notifying unit)
190 Display control unit
201 Right backlight control unit
202 Left backlight control unit
211 Right LCD control unit
212 Left LCD control unit
221 Right backlight
222 Left backlight
241 Right LCD
242 Left LCD
251 Right projection optical system
252 Left projection optical system
261 Right light guide plate
262 Left light guide plate
300 Information processing apparatus
310 First input-output unit
311 to 31$n$ First input-output units (acquiring units)
320 ROM
330 RAM
340 Communication interface
350 CPU
360 Generating unit
361 Specifying unit
370 Second input-output unit
371 to 37$n$ Second input-output units (providing units)
380 External storage device
381 Common video specification
382 Management table
383 Invisible information (invisible-information storing unit)
384 Record of operation
385 Position table (arrangement storing unit)
500 Medical apparatus
501 to 50$n$ Medical apparatuses
700 Display
1000 Information processing system
OA External apparatus
PC Personal computer
OD Database
VI Virtual image
PN Information for presentation
VR Visual field
PR Doctor
MP1 Position
UP1 Present position
CP1 Medical apparatus information

The invention claimed is:

1. An information processing apparatus comprising:
one or more processors programmed to:
receive an image captured from a camera of a head-mounted display apparatus;
automatically specify, by image recognition processing on the captured image, a medical apparatus as being difficult for a user of the head-mounted display apparatus to see, the medical apparatus that is difficult for the user to see being a medical apparatus that a display of which is absent from the captured image;
acquire, from the medical apparatus that is difficult to see, medical apparatus information;
generate information for presentation including at least a part of the acquired medical apparatus information; and
output the generated information for presentation.

2. The information processing apparatus according to claim 1, wherein the one or more processors are further programmed to:
acquire an image in a visual field direction of the user of the head-mounted display apparatus, and
perform the image recognition processing on the acquired image in the visual field direction of the user of the head-mounted display apparatus.

3. The information processing apparatus according to claim 1, wherein the one or more processors are further programmed to:
acquire position information for each of the plurality of medical apparatuses connected to the information processing apparatus,
acquire present position information representing a present position of the head-mounted display apparatus, and direction information representing a line-of-sight direction of a head of the user of the head-mounted display apparatus, and
automatically specify, by image recognition processing on the captured image, the medical apparatus as being difficult for the user of the head-mounted display to see, using the acquired position information of the plurality of medical apparatuses, the acquired present position information of the head-mounted display apparatus, and the acquired direction information of the head-mounted display apparatus.

4. The information processing apparatus according to claim 1, further comprising: a memory that stores information for specifying the medical apparatus that is difficult for the user of the head-mounted display to see, wherein the one or more processors are configured to: automatically specify the medical apparatus that is difficult for the user to see, using the stored information for specifying the medical apparatus that is difficult for the user of the head-mounted display to see.

5. The information processing apparatus according to claim 1, further comprising a memory that stores invisible information, which is information not appearing in an external appearance of an object, wherein the one or more processors are programmed to: include the invisible information in the generated information for presentation.

6. The information processing apparatus according to claim 1, wherein
at least one medical apparatus for acquiring invisible information, which is information not appearing in an external appearance of an object, is connected to the information processing apparatus, and
the one or more processors are further programmed to: include the invisible information in the generated information for presentation.

7. The information processing apparatus according to claim 1, wherein
at least one medical apparatus for acquiring an image of treatment of a patient is connected to the information processing apparatus, and
the one or more processors are further programmed to: include the image of treatment of the patient in the information for presentation.

8. The information processing apparatus according to claim 1, wherein the one or more processors are further programmed to: enlarge or reduce, in generating the information for presentation, an image included in the medical apparatus information while maintaining an aspect ratio of the image included in the medical apparatus information.

9. The information processing apparatus according to claim 1, further comprising: a medical apparatus communication interface configured to communicate with the medical apparatus that is difficult for the user to see.

10. The information processing apparatus according to claim 1, wherein the head-mounted display apparatus is configured to allow the user to simultaneously visually recognize a virtual image and an outside scene, and is connected to the information processing apparatus.

11. The information processing apparatus according to claim 10, wherein the one or more processors are further programmed to:
acquire, from the head-mounted display apparatus, an image in a visual field direction of the user in a state in which the head-mounted display apparatus is worn,
perform the image recognition processing on the acquired image in the visual field direction of the user to extract a characteristic of an object included in the outside scene,
correct, on the basis of the extracted characteristic, the generated information for presentation, and
output the corrected information for presentation.

12. An information processing method comprising:
receiving an image captured from a camera of a head-mounted display apparatus;
automatically specifying, by image recognition processing on the captured image, a medical apparatus as being difficult for a user of the head-mounted display apparatus to see, the medical apparatus that is difficult for the user to see being a medical apparatus that a display of which is absent from the captured image;
acquiring, from the medical apparatus that is difficult to see, medical apparatus information;
generating information for presentation including at least a part of the acquired medical apparatus information; and
outputting the generated information for presentation.

13. An information processing system comprising:
a plurality of medical apparatuses;
an information processing apparatus; and
a head-mounted display apparatus with which a user can simultaneously visually recognize a virtual image and an outside scene, wherein the information processing apparatus includes:
one or more processors programmed to:
receive an image captured from a camera of the head-mounted display apparatus;
automatically specify, by image recognition processing on the captured image, a medical apparatus of the plurality of medical apparatuses as being difficult for the user of the head-mounted display apparatus to see, the medical apparatus that is difficult for the user to see being a medical apparatus of the plurality of medical apparatuses that a display of which is absent from the captured image;

acquire, from the medical apparatus that is difficult to see, medical apparatus information;

generate information for presentation including at least a part of the acquired medical apparatus information; and output the generated information for presentation.

14. A head-mounted display apparatus that is connected to an information processing apparatus and with which a user of the head-mounted display apparatus can simultaneously visually recognize a virtual image and an outside scene, the head-mounted display apparatus comprising:

a camera configured to capture an image in a visual field direction of the user of the head-mounted display apparatus in a state in which the head-mounted display apparatus is worn; and a processor configured to:

perform image recognition processing on the acquired image in the visual field direction of the user, automatically specify, based on the performed image recognition processing on the captured image, a medical apparatus as being difficult for the user of the head-mounted display apparatus to see, the medical apparatus that is difficult for the user to see being a medical apparatus that a display of which is absent from the captured image;

notify the information processing apparatus of the specified medical apparatus;

acquire, from the information processing apparatus, information for presentation regarding the specified medical apparatus; and cause a display to display the acquired information for presentation as the virtual image.

\* \* \* \* \*